United States Patent
Bhansali et al.

(10) Patent No.: US 10,309,921 B2
(45) Date of Patent: Jun. 4, 2019

(54) LABEL-FREE ELECTROCHEMICAL BIOSENSOR

(71) Applicants: Shekhar Bhansali, Weston, FL (US); Abhay Vasudev Mallari, Hillsboro, OR (US)

(72) Inventors: Shekhar Bhansali, Weston, FL (US); Abhay Vasudev Mallari, Hillsboro, OR (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 424 days.

(21) Appl. No.: 14/636,758

(22) Filed: Mar. 3, 2015

(65) Prior Publication Data

US 2015/0247816 A1 Sep. 3, 2015

Related U.S. Application Data

(60) Provisional application No. 61/947,251, filed on Mar. 3, 2014.

(51) Int. Cl.
  *G01N 33/543* (2006.01)
  *G01N 27/327* (2006.01)

(52) U.S. Cl.
  CPC ..... *G01N 27/3275* (2013.01); *G01N 27/3271* (2013.01); *G01N 27/3272* (2013.01); *G01N 33/5438* (2013.01)

(58) Field of Classification Search
  None
  See application file for complete search history.

(56) References Cited

U.S. PATENT DOCUMENTS

| | | | | |
|---|---|---|---|---|
| 6,942,771 B1 * | 9/2005 | Kayyem | ............... | B01L 3/5027 204/409 |
| 2007/0054317 A1 * | 3/2007 | Diebold | ................ | C07F 15/002 435/7.1 |
| 2008/0251393 A1 * | 10/2008 | Estini | ....................... | B82Y 5/00 205/780.5 |

OTHER PUBLICATIONS

Vasudev et al. (Sensors and Actuators B: Chemical, 182, 139-146, available online Mar. 1, 2013).*

(Continued)

*Primary Examiner* — Gurpreet Kaur
*Assistant Examiner* — Steven E Rosenwald
(74) *Attorney, Agent, or Firm* — Saliwanchik, Lloyd & Eisenschenk

(57) ABSTRACT

The current invention pertains to electrochemical biosensors. The electrochemical biosensor of the current invention comprises:

a) a sensing electrode having attached to its surface a binding agent capable of specifically binding to the analyte to form a binding agent-analyte complex and wherein the binding of the analyte to the binding agent alters the electron transfer properties at the sensing electrode surface thereby providing a change in the electrochemical response at the sensing electrode surface proportional to the number of binding agent-analyte complexes, and b) a test equipment capable of measuring the electrochemical response at the sensing electrode surface.

The binding agent can be a binding protein, an antibody, or an aptamer, and the analyte can be a biomolecule. Accordingly, the current invention provides a method of detecting the presence or assessing the likelihood of development of a disease associated with an abnormal level of a biomolecule in a subject.

19 Claims, 29 Drawing Sheets

(56) References Cited

OTHER PUBLICATIONS

Ozkan et al. (Electrochem. Comm., 4, 2002, 796-802).*
Yang et al. (Analytical Letters, 45: 724-734, 2012, provided with this office action) (Year: 2012).*
Varkey et al. (Solar Energy Materials and Solar Cells 29, 253-259) (Year: 1993).*
Aardal, Elisabeth et al., "Cortisol in Saliva—Reference Ranges and Relation to Cortisol in Serum," *Eur J Clin Chem Clin Biochem*, 1995, 33:927-932.
Anandan, Venkataramani et al., "Nanopillar array structures for enhancing biosensing performance," *International Journal of Nanomedicine*, 2006, I(I):73-79.
Arya, Sunil K. et al., "Antibody functionalized interdigitated p-electrode (IDµE) based impedimetric cortisol biosensor," *Analyst*, 2010, 135:1941-1946.
Arya, Sunil K. et al., "Dithiobis(succinimidyl propionate) Modified Gold Micro Array Electrode Based Electrochemical Immunosensor for Ultrasensitive Detection of Cortisol," *Biosens Bioelectron*, Jun. 2010, 25(10):2296-2301.
Arya, Sunil K. etal., "Polyaniline protected gold nanoparticles based mediator and label free electrochemical cortisol biosensor," *Biosensors and Bioelectronics*, 2011, 28:166-173.
Atashbar, Massood Z. et al., "Qcm biosensor with ultra thin polymer film," *Sensors and Actuators B*, 2005, 107:945-951.
Bembnowicz, Pawel et al., "Preliminary studies on LTCC based PCR microreactor," *Sensors and Actuators B*, 2010, 150:715-721.
Birol, Hansu et al., "Application of graphite-based sacrificial layers for fabrication of LTCC (low temperature co-fired ceramic) membranes and microchannels," *Journal of Micromechanics and Microengineering*, 2007, 17(1):50-60.
Carrozza, C. et al., "Clinical accuracy of midnight salivary cortisol measured by automated electrochemiluminescence immunoassay method in Cushing's syndrome," *Ann Clin Biochem*, May 2010, 47(Part 3):Abstract.
Cecchi, A. et al., "Environmental exposure to organophosphate pesticides: Assessment of endocrine disruption and hepatotoxicity in pregnant women," *Ecotoxicol. Environ. Saf.*, 2012, pp. 1-8.
De Kloet, E. Ron et al., "Stress and the Brain: From Adaptation to Disease," *Nature Reviews*: Neuroscience, Jun. 2005, 6:463-475.
De Palo, Elio F. et al., "Human saliva cortisone and cortisol simultaneous analysis using reverse phase HPLC technique," *Clinica Chimica Acta*, 2009, 405:60-65.
Delahanty, Douglas L. et al., "Initial Posttraumatic Urinary Cortisol Levels Predict Subsequent PTSD Symptoms in Motor Vehicle Accident Victims," *Biol Psychiatry*, 2000, 48:940-947.
Djuric, Zora et al., "Biomarkers of Psychological Stress in Health Disparities," *Open Biomark J.*, Jan. 2008, 1:7-19.
Farhan Shafique, M. et al., "Fabrication of embedded microfluidic channels in low temperature co-fired ceramic technology using laser machining and progressive lamination," *Journal of European Ceramic Society*, Nov. 2011, pp. 1-6.
Gao, Wei et al., "HPLC-FLU detection of cortisol distribution in human hair," *Clinical Biochemistry*, 2010, 43:677-682.
Gatti, Rosalba et al., "Cortisol assays and diagnostic laboratory procedures in human biological fluids," *Clinical Biochemistry*, 2009, 42:1205-1217.
Gongora-Rubio, M.R. et al., "Overview of low temperature co-® red ceramics tape technology for meso-system technology (MsST)," *Sensors and Actuators A*, 2001, 89:222-241.
Hellhammer, Dirk H. et al., "Salivary cortisol as a biomarker in stress research," *Psychoneuroendocrinology*, 2009, 34:163-171.
Ibañez-García, Núria etal., "Green-tape ceramics. New technological approach for integrating electronics and fluidics in microsystems," *Trends in Analytical Chemistry*, 2008, 27(1):24-33.
Kaushik, Ajeet et al., "Mediator and label free estimation of stress biomarker using electrophoretically deposited Ag@AgO-polyaniline hybrid nanocomposite," *Biosensors and Bioelectronics*, 2013, 50:35-41.
Kaushik, Ajeet et al., "Recent advances in cortisol sensing technologies for point-of-care application," *Biosensors and Bioelectronics*, 2014, 53:499-512.
Klopfenstein, Bethany J. et al., "Determination of cortisol production rates with contemporary liquid chromatography-mass spectrometry to measure cortisol-$d_3$ dilution after infusion of deuterated tracer," *Clin Biochem.*, Apr. 2011, 44(5-6):430-434.
Kumar, Arun et al., "Ultrasensitive detection of cortisol with enzyme fragment complementation technology using functionalized nanowire," *Biosensors and Bioelectronics*, 2007, 22:2138-2144.
Lac, G. et al., "Elevated salivary cortisol levels as a result of sleep deprivation in a shift worker," *Occupational Medicine*, 2003, 53:143-145.
Lamond, N. et al., "The impact of a week of simulated night work on sleep, circadian phase, and performance," *Occup Environ Med*, 2003, 60(e13):1-9.
Levine, Ari etal., "Measuring cortisol in human psychobiological studies," *Physiology & Behavior*, 2007, 90:43-53.
Lewis, J.G. et al., "Fractionation of Cortisol Antisera by Immunoadsorption Chromatography: Characterisation and Use in an Enzyme-Linked Immunosorbent Assay (ELISA)," *J. Steroid Biochem.*, 1985, 22(3):387-390.
Lippi, Giuseppe et al., "Measurement of morning saliva cortisol in athletes," *Clinical Biochemistry*, 2009, 42:904-906.
Loncaric, Carlyn et al., "A USB-based electrochemical biosensor prototype for point-of-care diagnosis," *Sensors and Actuators B*, 2012, 161:908-913.
Lupien, Sonia J. etal., "Effects of stress throughout the lifespan on the brain, behavior and cognition," *Nature Reviews: Neuroscience*, Jun. 2009, 10:434-445.
Malecha, Karol et al., "LTCC Microfluidic Systems for Biochemical Diagnosis," *Biocybernetics and Biomedical Engineering*, 2011, 31(4):31-41.
Manenschijn, Laura et al., "Evaluation of a method to measure long term cortisol levels," *Steroids*, 2011, 76:1032-1036.
Mangold, Deborah et al., "Acculturation, Childhood Trauma and the Cortisol Awakening Response in Mexican American Adults," *Horm Behav.*, Sep. 2010, 58(4):637-646.
Mangold, Deborah et al., "The Cortisol Awakening Response Predicts Subclinical Depressive Symptomatology in Mexican American Adults," *J Psychiatr Res.*, Jul. 2011, 45(7):902-909.
McEwen, Bruce S. "Editorial: Cortisol, Cushing's Syndrome, and a Shrinking Brain—New Evidence for Reversibility," *The Journal of Clinical Endocrinology & Metabolism*, 2002, 87(5):1947-1948.
Shankaran, Dhesingh Ravi et al., "Recent advancements in surface plasmon resonance immunosensors for detection of small molecules of biomedical, food and environmental interest," *Sensors and Actuators B*, 2007, 121:158-177.
Shi, Hongmei et al., "Determination of cortisol in human blood sera by a new Ag(III) complex—luminol chemiluminescent system," *Analytical Biochemistry*, 2009, 387:178-183.
Small, Brian C. et al., "Validation of a Time-Resolved Fluoroimmunoassay for Measuring Plasma Cortisol in Channel Catfish lctalurus punctatus," *Journal of the World Aquaculture Society*, Jun. 2002, 33(2):184-187.
Stevens, Richard C. et al, "Detection of cortisol in saliva with a flow-filtered, portable surface plasmon resonance biosensor system," *Anal Chem.*, Sep. 2008, 80(17):6747-6751.
Van Aken, Maarten O. et al., "Automated Measurement of Salivary Cortisol," *Technical Briefs, Clinical Chemistry*, 2003, 49(8):1408-1409.
Vasudev, Abhay et al., "Prospects of low temperature co-fired ceramic (LTCC) based microfluidic systems for point-of-care biosensing and environmental sensing," *Microfluidics and Nanotluidics*, Nov. 2012, pp. 1-22.
Venugopal, Manju et al., "A realtime and continuous assessment of cortisol in ISF using electrochemical impedance spectroscopy," *Sensors and Actuators A*, 2011, 172:154-160.
Vogeser, Michael et al., "Free serum cortisol: quantification applying equilibrium dialysis or ultrafiltration and an automated immunoassay system," *Clin Chem Lab Med*, 2007, 45(4):521-525.

(56) References Cited

OTHER PUBLICATIONS

Wan, Ying et al., "Development of electrochemical immunosensors towards point of care diagnostics," *Biosensors and Bioelectronics*, 2013, 47:1-11.

Wang, Joseph. "Electrochemical biosensors: Towards point-of-care cancer diagnostics," *Biosensors and Bioelectronics*, 2006, 21:1887-1892.

Whitesides, George M. "The origins and the future of microfluidics," *Nature*, Jul. 2006, 442:368-373.

Yamaguchi, Masaki et al., "Innmunosensor with Fluid Control Mechanism for Salivary Cortisol Analysis," *Biosens Bioelectron.*, Mar. 2013, 41:186-191.

Yehuda, Rachel et al., "Childhood trauma and risk for PTSD: Relationship to intergenerational effects of trauma, parental PTSD, and cortisol excretion," *Development and Psychopathology*, 2001, 13:733-753.

Yehuda, Rachel et al., "Cortisol levels in adult offspring of Holocaust survivors: relation to PTSD symptom severity in the parent and child," *Psychoneuroendocrinology*, 2007, 27:171-180.

Kaushik, A. et al., "A label-free electrochemical immunosensor for beta-amyloid detection." *Analytical Methods*, 2016, 8: 6115-6120, DOI: 10.1039/c6ay01910b.

Kaushik, A. et al., "Electrochemical sensing method for point-of-care cortisol detection in human immunodeficiency virus-infected patients." *International Journal of Nanomedicine*, 2015, 10: 1-9.

Pasha, S. K., et al., "Electrochemical Immunosensing of Saliva Cortisol." *Journal of the Electrochemical Society*, 2014, 161(2): B3077-B3082, DOI: 10.1149/2.017402jes.

\* cited by examiner

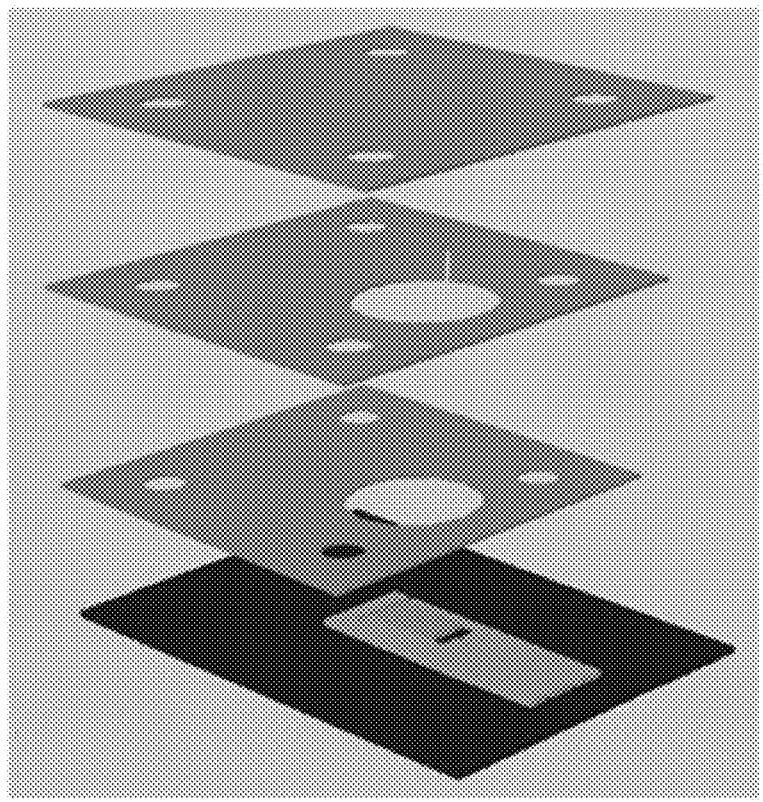
FIG. 3C
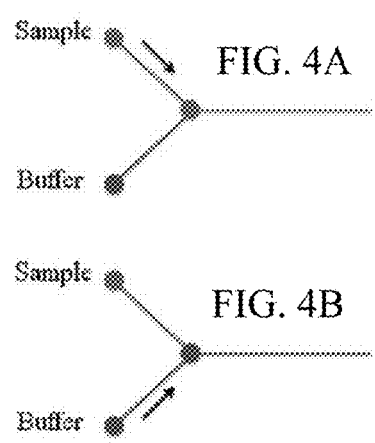
FIG. 4A
FIG. 4B
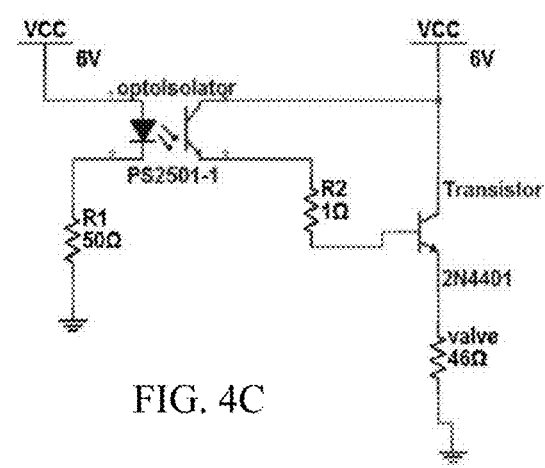
FIG. 4C

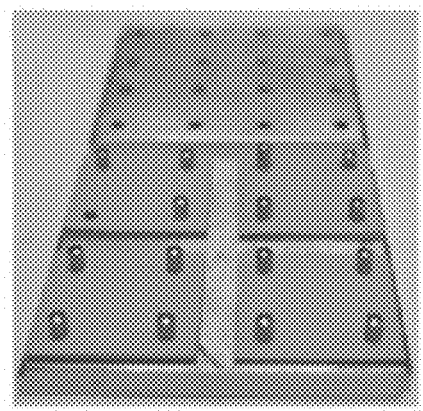
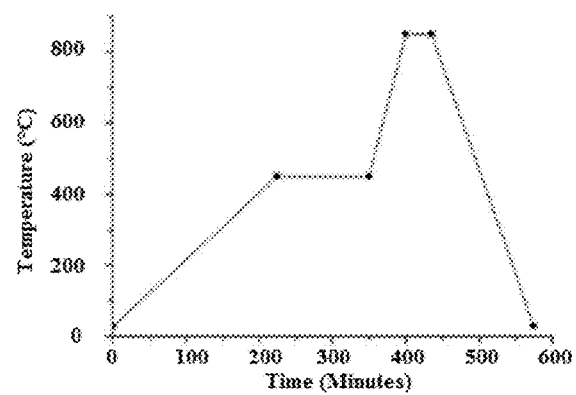
FIG. 5A  FIG. 5B
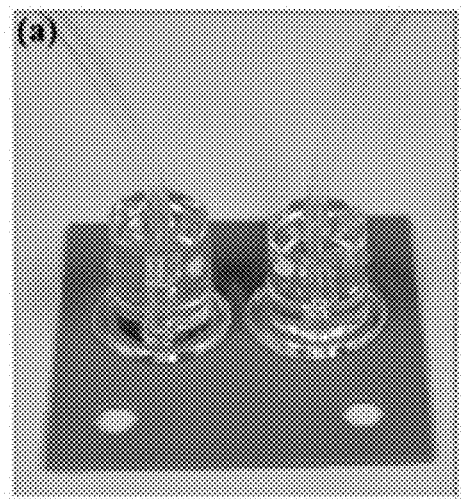
FIG. 6A

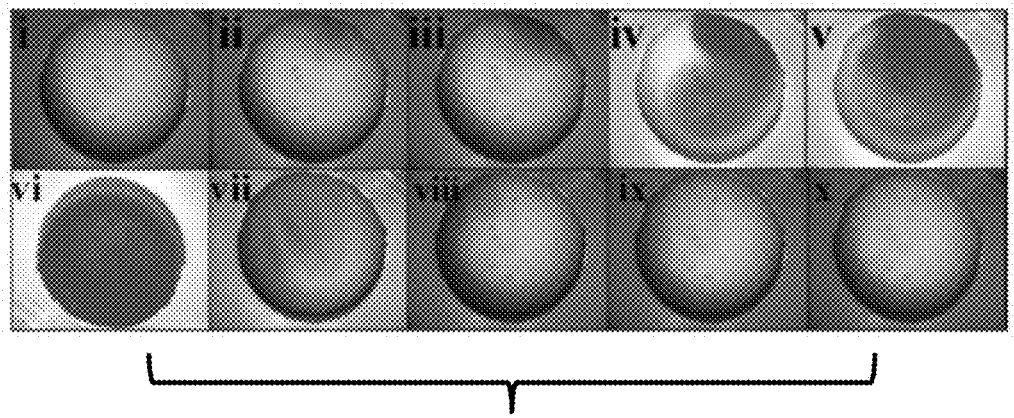
FIG. 7C
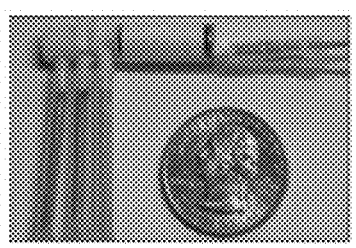   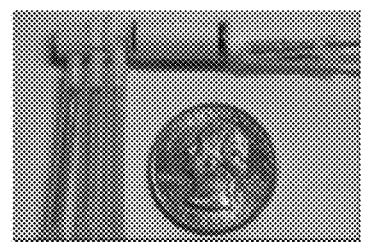
FIG. 8A            FIG. 8B
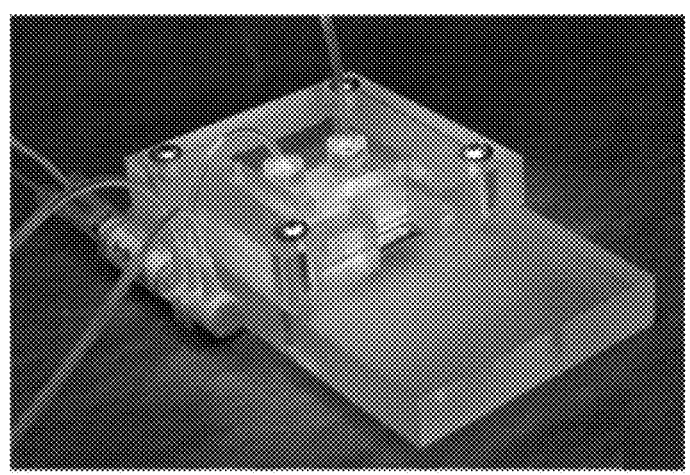
FIG. 8C

LABEL-FREE ELECTROCHEMICAL BIOSENSOR

CROSS-REFERENCE TO RELATED APPLICATIONS

This application claims the priority benefit of U.S. Provisional Application Ser. No. 61/947,251, filed Mar. 3, 2014, which is incorporated herein by reference in its entirety.

GOVERNMENT SUPPORT

The subject invention was made with government support under a research project supported by the National Science Foundation under Award Number EEC-1160483. The government has certain rights in this invention.

BACKGROUND OF INVENTION

Systems for monitoring physiological variables on a daily basis at point-of-care (POC) are deemed as the cornerstone technology for improved health care delivery at reduced costs. ELISA and other laboratory techniques such as high performance liquid chromatography, surface plasma resonance, and equilibrium dialysis are the prevailing methods for monitoring physiological variables in the current state of the art. Most of these techniques do not lend themselves well to miniaturized automated systems for application at POC.

Therefore, POC systems that can quantify critical physiological parameters can enable better diagnosis and better treatment strategies. Many of the current sensing systems that are used in diagnostic laboratories cannot be applied at POC due to constraints of portability, cost, analysis time, and requirement of highly skilled personnel to operate these systems. Microfluidic systems have enabled the development of POC chemical and biological assays. The main advantages of microfluidic systems are small sample volumes, precise control of fluidic routines, repeatable sensing protocols, controlled environment for bio-molecule reaction, reduced form factor, and application at point of care. The high degree of automation that exists in microfluidic systems also eliminates error often associated with human handling and thereby reduces the percentage of inaccurate results.

BRIEF SUMMARY

The current invention integrates biosensors into microfluidic devices to provide novel POC electrochemical biosensors. The current invention provides design, fabrication and testing of a microfluidic system that is coupled with a disposable biosensor for the detection of analytes, for example biomolecules. In the current invention, an analyte is detected on an electrochemical biosensing platform, which is based on binding agent-analyte interaction that provides the specific and selective detection of a target analyte. Electrochemical transduction techniques are highly sensitive and rapid, and require only simple electrical circuits for signal acquisition.

Accordingly, an embodiment of the current invention provides an electrochemical biosensor for measuring concentration of an analyte in a fluid. The electrochemical biosensor of the current invention comprises:

a) a sensing electrode having attached to its surface a binding agent capable of specifically binding to the analyte to form a binding agent-analyte complex and wherein the binding of the analyte to the binding agent alters the electron transfer properties at the sensing electrode surface thereby providing a change in the electrochemical response at the sensing electrode surface proportional to the number of binding agent-analyte complexes, and b) a test equipment capable of measuring the electrochemical response at the sensing electrode surface.

The test equipment can measure the electrochemical response, for example, increased electrical resistance, at the sensing electrode surface. The test equipment can be a voltmeter, ohmmeter, ammeter, multimeter, potentiostat, or a cyclic voltmeter.

The current invention also provides a method of measuring concentration of an analyte in a fluid using the electrochemical biosensor of the current invention. The method of the current invention comprises contacting the sensing electrode of the electrochemical biosensor with the fluid under conditions that allow the formation of the binding agent-analyte complexes for a period of time sufficient to allow the formation of the binding agent-analyte complexes, washing the sensing electrode with a washing solution to remove unbound and non-specifically bound chemicals from the sensing electrodes, introducing a detection solution over the sensing electrode, measuring the electrochemical response at the sensing electrode surface, and calculating the concentration of the analyte in the fluid based on the electrochemical response at the sensing electrode surface.

In the methods of the current invention, the sensing electrode can be disposable, the binding agent of the electrochemical biosensor can be a binding protein, an antibody, or an aptamer, the analyte can be a biomolecule, for example, a hormone, a protein, a polysaccharide, a lipid, a polynucleotide, or a metabolite, and the fluid can be a biofluid. Accordingly, the current invention also provides a method of detecting the presence of a disease or assessing the likelihood of development of the disease associated with abnormal levels of a biomolecule in a subject. The method of detecting the presence or assessing the likelihood of development of the disease according to the current invention comprises: obtaining a biofluid from a subject, contacting the sensing electrode of the electrochemical biosensor with a biofluid under conditions that allow the formation of the binding agent-biomolecule complexes for a period of time sufficient to allow the formation of the binding agent-biomolecule complexes, washing the sensing electrode with a washing solution to remove unbound and non-specifically bound chemicals from the sensing electrode, introducing a detection solution over the sensing electrode, measuring the electrochemical response at the sensing electrode surface, calculating the concentration of the biomolecule in the biofluid based on the electrochemical response at the sensing electrode surface, and identifying the subject as having the disease or having an increased likelihood of developing the disease if the concentration of the biomolecule in the biofluid is abnormal.

BRIEF DESCRIPTION OF THE DRAWINGS

In order that a more precise understanding of the above recited invention can be obtained, a more particular description of the invention briefly described above will be rendered by reference to specific embodiments thereof that are illustrated in the appended drawings. Thus, understanding that these drawings depict only typical embodiments of the invention and are not therefore to be considered as limiting in scope, the invention will be described and explained with additional specificity and detail through the use of the accompanying drawings.

This patent or application file contains at least one drawing executed in color. Copies of this patent or patent application publication, with color drawing(s), will be provided by the Office upon request and payment of the necessary fee.

FIGS. 3A-3C. Schematic illustration of the low temperature co-fired ceramic (LTCC) based electrochemical biosensor; (b) the three-layer design of the LTCC microfluidic manifold; (c) a 3D blow out of the microfluidic chip and its integration with the sensor electrode chip.

FIGS. 4A-4C. Schematic of the operation of the fluidic valve; (c) schematic of the electronic circuit designed for the activation of the fluidic valve.

FIGS. 5A-5B. (a) Picture of the aligning fixture with LTCC tapes being aligned prior to lamination; (b) the temperature ramping profile for the sintering process.

FIGS. 6A-6B. (a) The LTCC microfluidic manifold; (b) cross sectional microscopic image of the LTCC microchannel.

FIGS. 7A-7C. (a) Schematic of the LTCC microfluidic chip used for fluid flow characterization; (b) picture of the glass window integrated into the LTCC chip; (c) microscopic images of the fluid flow profiles in the assay chamber.

FIGS. 8A-8C. (a and b) Characterization of the valving function in the fluidic valve; (c) picture of the fully integrated microfluidic system with fluid valve, microfluidic manifold and the sensing electrode chip.

DETAILED DISCLOSURE

Figure 1A:
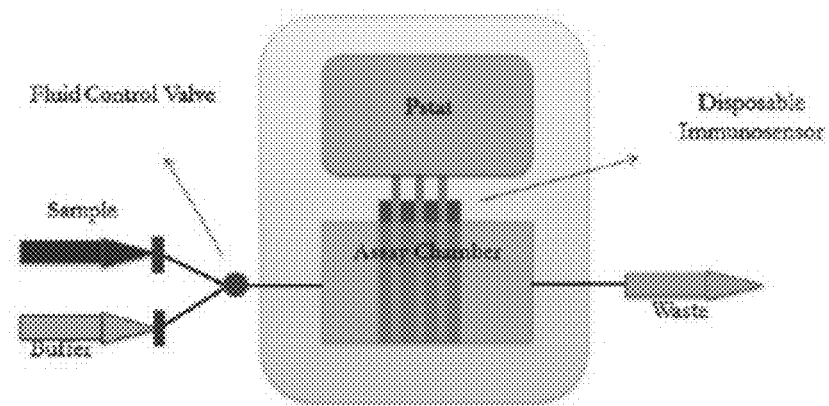
FIGS. 1A-1B. (a) Concept design of an example of the electrochemical biosensor. (b) Schematic illustration of the interdigitated Au microelectrode with proposed biofunctionalization scheme (inset) for detection of Cortisol.

The term "about" is used in this patent application to describe some quantitative aspects of the invention, for example, concentration. It should be understood that absolute accuracy is not required with respect to those aspects for the invention to operate. When the term "about" is used to describe a quantitative aspect of the invention the relevant aspect may be varied by ±10% (e.g., ±1%, ±2%, ±3%, ±4%, ±5%, ±6%, ±7%, ±8%, ±9%, or ±10%).

The current invention provides an electrochemical biosensor for measuring concentration of an analyte in a fluid. The electrochemical biosensor comprises:

a) a sensing electrode having attached to its surface a binding agent capable of specifically binding to the analyte to form a binding agent-analyte complex and wherein the binding of the analyte to the binding agent alters the electron transfer properties at the sensing electrode surface thereby providing a change in the electrochemical response at the sensing electrode surface proportional to the number of binding agent-analyte complexes, and b) a test equipment capable of measuring the electrochemical response at the sensing electrode surface.

The sensing electrode of the current invention is designed based on the principles of electrochemical biosensing. Electrochemical biosensing involves measuring the changes in electrochemical properties, for example, electron transfer properties, of a conductive material due to the adsorption of an analyte on the surface of the conductive material to which binding agents for the analyte are attached. The changes in the electrochemical properties are attributed to the changes in the transfer of electrons from redox active species from the solution surrounding the biosensing electrode and at the surface of the biosensing electrode. For example, during biosensing reaction, the binding of an analyte to the binding agent attached to the sensing electrode surface produces binding agent-analyte complexes that block the electron transport from the redox species in the fluid to the sensing electrode surface which causes reduced electric current at the sensing electrode surface. Also, greater the number of binding agent-analyte complexes, greater is the blocking of the electron transport from the redox species in the fluid to the sensing electrode surface and greater is the reduction in the current from the sensing electrode surface. Therefore, reduction in the electric current at the sensing electrode surface can be correlated to the concentration of the analyte molecules bound to the binding agent attached to the sensing electrode surface.

In an embodiment of the current invention, the sensing electrode is fabricated from a material which does not readily interact with other chemicals, for example, chemicals routinely used in fluid media used to analyze soluble analytes. In certain embodiments, the sensing electrode can be fabricated from noble metals.

For the purposes of the current invention, a noble metal is a metal that resists chemical reaction, for example, oxidation, resists corrosion, and is not easily attacked by acids. A noble metal as used herein includes noble metals and alloys thereof. Non-limiting examples of noble metals that can be used in the current invention include copper, silver, platinum, gold, bismuth, palladium, osmium, iridium, ruthenium, and rhodium. Additional examples noble metals that can be used in the current invention are well known to a person of ordinary skill in the art and such embodiments are within the purview of the current invention.

In one embodiment, the sensing electrode is in the form of an interdigitated microelectrode (IDE). In one embodiment, the IDE type sensing electrode comprises Au electrodes wherein the interdigitated array comprise about 15 µm wide electrode fingers at a pitch of about 15 µm in an area of about 5 mm×5 mm (FIG. 1b). Additional architectural variations of IDE, for example, the length of the electrode fingers and the pitch can be envisioned by a person of ordinary skill in the art and such variations are within the purview of the current invention. Additionally, different geometric variations of IDE, for example, circular IDE, are also within the purview of the current invention.

In an embodiment of the invention the binding agent is capable of specifically binding to the analyte to be measured. For the purposes of this invention, the binding between two molecules based on specific interactions between specific sites present on the two molecules is referred to as "specific binding." Specific binding between two entities are scientifically represented by their dissociation constant that are often less than about $10^{-6}$ M, less than about $10^{-7}$ M, or less than about $10^{-8}$ M. Examples of specific binding include, but are not limited to, binding between an antibody and the corresponding antigen based on the interactions between the paratope of the antibody and epitope on the antigen and the binding between an aptamer and its target biomolecule based on the interactions between the target binding sites present on the aptamer and the binding site present on the target biomolecule. Additional examples of specific binding between any two molecules, for example, biomolecules, and further aspects of specific binding are well known to a person of ordinary skill in the art and such embodiments are within the purview of the current invention.

In an embodiment of the current invention, the binding agent is a protein, for example, an antibody, that can specifically bind to an analyte, for example, the corresponding antigen. In certain other embodiments, the protein can be an antibody or a fragment thereof. Non-limiting examples of antibodies or antibody fragments that can be used in the current invention include monoclonal antibodies, polyclonal antibodies, humanized antibodies, fragment antigen-binding (Fab fragment), single-chain variable fragment (scFv), diabodies, triabodies, minibodies, and single-domain antibodies. Additional examples antibodies or fragments thereof that can be used in the current invention are well known to a person of ordinary skill in the art and such embodiments are within the purview of the current invention. In a further embodiment, the binding site can be a protein receptor, a protein aptamer, or a protein binding partner of a biomolecule. Additional examples of binding agents that can be used in the current invention are well known to a person of ordinary skill in the art and such embodiments are within the purview of the current invention.

The sensing electrode of the current invention has the binding agent attached to its surface. In one embodiment, one or more different types of binding agents capable of specifically binding to the same analyte are attached to the sensing electrode surface. For example, a combination of an antibody and an aptamer capable of specifically binding to a biomolecule can be attached to the sensing electrode surface.

The binding agent can be attached to the sensing electrode surface in various ways. In certain embodiments, the binding agent is attached to the sensing electrode surface in a covalent manner. Binding in a covalent manner ensures that the binding agent is, for practical purposes, permanently attached to the sensing electrode which avoids the loss of the binding agent, for example, during the washing of the sensing electrode. In another embodiment, the binding agent is attached to the sensing electrode surface in a non-covalent manner.

In one embodiment, the binding agent is attached to the sensing electrode using a self-assembled monolayer (SAM) of dithiobissuccinimidyl propionate (DTSP) as the immobilizing matrix. Additional examples of attaching a binding agent to the sensing electrode surface are well known to a person of ordinary skill in the art and such embodiments are within the purview of the claimed invention.

The changes in the electrochemical properties, for example, electron transfer properties, at the sensing electrode surface upon binding of the analyte to the binding agent attached to the sensing electrode surface can be measured by a test equipment. Various electrochemical properties at the sensing electrode surface that can be measured by the test equipment include, but are not limited to, electrical resistance and current. In certain embodiments, the test equipment is voltmeter, ohmmeter, ammeter, multimeter, or a potentiostat. In a further embodiment, the test equipment is a cyclic voltmeter.

An aspect of the current invention provides a method of measuring concentration of an analyte in a fluid using the electrochemical biosensor of the current invention. The method of measuring concentration of an analyte in a fluid comprises:
 a) providing an electrochemical biosensor comprising:
  A) a sensing electrode having attached to its surface a binding agent capable of specifically binding to the analyte to form a binding agent-analyte complex and wherein the binding of the analyte to the binding agent alters the electron transfer properties at the sensing electrode surface thereby providing a change in the electrochemical response at the sensing electrode surface proportional to the number of binding agent-analyte complexes, and
  B) a test equipment which measures the electrochemical response at the sensing electrode surface,
 b) contacting the sensing electrode with the fluid under conditions that allow the formation of the binding agent-analyte complexes for a period of time sufficient to allow the formation of the binding agent-analyte complexes,
 c) washing the sensing electrode with a washing solution to remove unbound and non-specifically bound chemicals from the sensing electrode,
 d) introducing a detection solution over the sensing electrode,
 e) measuring the electrochemical response at the sensing electrode surface, and
 f) calculating the concentration of the analyte in the fluid based on the electrochemical response at the sensing electrode surface.

In the method of the current invention the fluid containing the analyte to be measured is contacted with the sensing electrode under conditions that allow the formation of the binding agent-analyte complexes for a period of time sufficient to allow the formation of the binding agent-analyte complexes. In a preferred embodiment, the fluid containing the analyte to be measured is contacted with the sensing electrode under conditions that allow or promote only specific binding between the binding agent and the analyte in the solution and optionally, inhibiting the non-specific binding between the binding agent and other chemicals in the fluid.

A period of time sufficient to allow the formation of the binding agent-analyte complexes can be about 1 minute to about 60 minutes, about 5 minutes to about 50 minutes, about 10 minutes to about 40 minutes, about 10 minutes to about 30 minutes, about 30 minutes, or about 10 minutes.

The conditions that allow or promote specific binding between the binding agent and the analyte include, but are not limited to, absence/presence and concentration of specific chemicals or biomolecules, surfactants, a buffer such as phosphate buffered saline (PBS), pH of the solution, temperature of the solution, or a combination of these conditions.

After contacting the fluid containing the analyte with the sensing electrode the method of the current invention further includes washing the sensing electrode with a washing solution to remove unbound and non-specifically bound chemicals from the sensing electrode. This step permits only the analyte to be measured to remain bound to the binding agents on the sensing electrode surface and removes chemicals unbound or non-specifically bound to the binding agents. In an embodiment of the invention, the washing solution is PBS optionally containing a surfactant such as Tween or sodium dodecyl sulfate.

For the purposes of this invention, the binding between two molecules which is not based on specific interactions between the two molecules is referred to as "non-specific binding". Examples of non-specific binding include, but are not limited to, binding between an antibody and an antigen which is not a target antigen for the antibody and the binding is based on the interactions between the random sites on the antibody and the antigen, binding between an aptamer and a biomolecule which is not the target biomolecule for the aptamer and the binding is based on the interactions between random sites present on the aptamer and the biomolecule. Additional examples of non-specific binding between any two molecules and further aspects of non-specific binding are well known to a person of ordinary skill in the art.

In a preferred embodiment, the sensing electrode is washed with a washing solution under conditions that allow or promote only specific binding between the binding agent and the analyte in the solution and remove the chemicals that are non-specifically bound to the binding agent. Non-limiting example of chemicals that can non-specifically bind to binding agents include molecules structurally related but different from the analyte to be measured. The conditions that promote removal of the chemicals that are non-specifically bound to the binding agent include, but are not limited to, absence/presence and concentration of specific chemicals or biomolecules, surfactants, a buffer such as PBS (phosphate buffered saline), pH of the solution, temperature of the solution, shear stress of washing solution, or a combination of these conditions.

After the non-specifically bound chemicals are removed from the sensing electrode, the method of the current invention involves introducing a detection solution over the sensing electrode. The detection provides electro active redox species that can exchange electrons with the sensing electrode. If the amount of the analyte in the fluid is low, a lower number of binding agent-analyte complexes are formed, and a higher number of electrons are exchanged between the sensing electrode surface and the detection solution. On the other hand, if the amount of the analyte in the fluid is high, a higher number of binding agent-analyte complexes are formed, and a lower number of electrons are exchanged between the sensing electrode surface and the detection solution. In one embodiment of the invention, the redox species used in the detection solution is $[Fe(CN)_6]^{3-/4-}$. In another embodiment, the detection solution is phosphate buffer saline (PBS) containing 5 mM $[Fe(CN)_6]^{3-/4-}$. Additional examples of redox species that can be used in the detection solution of the current invention can be envisioned by a person of ordinary skill in the art and such embodiments are within the purview of the current invention.

After a detection solution is introduced over the sensing electrode, the method of the current invention further comprises measuring the electrochemical response at the sensing electrode surface. Measuring the electrochemical response at the sensing electrode surface is performed by the test equipment. Aspects of the test equipment discussed above in connection with the electrochemical biosensor of the current invention are also applicable to the method of measuring concentration of an analyte in a fluid using the electrochemical biosensor of the current invention.

The method of the current invention further includes calculating the concentration of the analyte in the fluid based on the electrochemical response at the sensing electrode surface. A number of methods can be used to calculate the concentration of the analyte in the fluid.

For example, a predetermined calibration curve of the electrochemical response obtained from control fluids containing known concentrations of the analyte can be used to extrapolate the concentration of the analyte in the tested fluid. Alternately, the electrochemical response at the sensing electrode surface before the binding of the analyte can be compared with the electrochemical response at the sensing electrode surface after the binding of the analyte. The concentration of the analyte can then be measured based on the difference between the electrochemical response at the sensing electrode surface before and after the binding of the analyte. Additional methods of measuring the concentration of the analyte based on the electrochemical response at the sensing electrode surface after the binding of the analyte are well known to a person of ordinary skill in the art and such embodiments are within the purview of the current invention.

In one embodiment of the current invention, the method comprises measuring concentration of a biomolecule. Non-limiting examples of the biomolecules that can be measured according to the methods of the current invention include a hormone, a protein, a polysaccharide, a lipid, a polynucleotide, or a metabolite. The binding agent used in the sensing electrode can be changed based on the biomolecule to be measured. For example, for measurement of a protein in a fluid, an antibody or another protein capable of specifically binding to the protein can be attached to the sensing electrode surface. For measurement of a metabolite, an enzyme binding to the metabolite can be attached to the sensing electrode surface. Additional combinations of biomolecules and their corresponding binding agents are well known to a person of ordinary skill in the art and such embodiments are within the purview of the current invention.

In one embodiment of the current invention, the biomolecule is a hormone, for example, a steroid hormone or a peptide hormone. In a further embodiment, an antibody specifically binding to the steroid hormone or the peptide hormone is attached to the sensing electrode surface. In an even further embodiment of the invention, a receptor protein to which the hormone specifically binds is attached to the sensing electrode surface.

Non-limiting examples of the peptide hormones that can be detected by the current invention include Thyroid-stimulating hormone (TSH), Follicle-stimulating hormone (FSH), Luteinizing hormone (LH), Prolactin (PRL), Growth hormone (GH), Adrenocorticotropic hormone (ACTH), Vasopressin, Oxytocin, Thyrotropin-releasing hormone (TRH), Gonadotropin-releasing hormone (GnRH), Growth hormone-releasing hormone (GHRH), Corticotropin-releasing hormone (CRH), Somatostatin, Calcitonin, Parathyroid hormone (PTH), FGF-23 (phosphatonin), Osteocalcin, Erythropoietin (EPO), Human chorionic gonadotropin (HCG), Insulin, Glucagon, Somatostatin, Amylin, Atrial-natriuretic peptide (ANP), Gastrin, Secretin, Cholecystokinin (CCK), Fibroblast Growth Factor 19 (FGF19), Incretins, Somatostatin, Neuropeptide Y, Ghrelin, PYY3-36, Insulin-like growth factor-1 (IGF-1), Angiotensinogen, Thrombopoietin, Hepcidin, Betatrophin, Leptin, Retinol Binding Protein 4, Adiponectin, Irisin. Non-limiting examples of steroid hormones that can be detected by the current invention include progesterone, aldosterone, testosterone, estradiol, and Cortisol. Additional examples of hormones that can be measured according to the current invention are well known to a person of ordinary skill in the art and such embodiments are within the purview of the current invention.

In one embodiment of the invention, the biomolecule is a metabolite, for example, a steroid such as cholesterol.

In one embodiment of the invention, the biomolecule measured by the method of the current invention is associated with the presence or the likelihood of development of the disease in a subject. For example, the presence or the likelihood of development of the disease in a subject can be associated with an abnormal level of the biomolecule in a sample, for example, a biofluid sample, obtained from the subject. Also, the electrochemical biosensor can be disposable, for example, in the form of a disposable chip. Accordingly, the current invention also provides a method of detecting the presence or assessing the likelihood of development of a disease in a subject wherein the disease is associated with an abnormal level of a biomolecule in a sample obtained from the subject. The subject can be an animal, for example, a mammal such as a human, a primate, a bovine, a pig, a feline, a rodent, or a canine.

The method of detecting the presence or assessing the likelihood of development of a disease in a subject, wherein the disease is associated with an abnormal level of a biomolecule comprises:

a) providing an electrochemical biosensor comprising:
  A) a sensing electrode having attached to its surface a binding agent capable of specifically binding to the biomolecule to form a binding agent-biomolecule complex wherein the binding of the biomolecule to the binding agent alters the electron transfer properties at the sensing electrode surface thereby providing a change in the electrochemical response at the sensing electrode surface proportional to the number of binding agent-biomolecule complexes, and
  B) a test equipment which measures the electrochemical response at the sensing electrode surface, b) contacting the sensing electrode with the biofluid under conditions that allow the formation of the binding agent-biomolecule complexes for a period of time sufficient to allow the formation of the binding agent-biomolecule complexes, c) washing the sensing electrode with a washing solution to remove unbound and non-specifically bound chemicals from the sensing electrode, d) introducing a detection solution over the sensing electrode, e) measuring the electrochemical response at the sensing electrode surface, f) calculating the concentration of the biomolecule in the biofluid based on the electrochemical response at the sensing electrode surface, and g) identifying the subject as having the disease or having an increased likelihood of developing the disease if the concentration of the biomolecule in the biofluid is abnormal.

Non-limiting examples of biofluids that can be subjected to the methods of current invention include amniotic fluid, aqueous humor, vitreous humor, bile, cerebrospinal fluid, chyle, endolymph, perilymph, female ejaculate, male ejaculate, lymph, mucus (including nasal drainage and phlegm), pericardial fluid, peritoneal fluid, pleural fluid, pus, rheum, saliva, sputum, synovial fluid, vaginal secretion, and blood. The biofluid can be processed prior to analysis according to the current invention. For example, blood can be processed to make it suitable for analysis by the electrochemical biosensor of the current invention, for example, by removal of the cells or by deprotenization.

A biofluid sample according to the current invention also includes tissue extracts, for example, a liver extract. The tissue that can be examined according to the current invention include, but is not limited to, brain, eyes, Pineal gland, Pituitary gland, Thyroid gland, Parathyroid glands, thorax, heart, lungs, esophagus, Thymus, pleura, Adrenal glands, Appendix, Gall bladder, urinary bladder, large intestine, small intestine, kidneys, liver, pancreas, spleen, stoma, Prostate gland, testes, ovaries, or uterus.

A tissue can be processed to make it suitable for analysis by the electrochemical biosensor of the current invention. Non-limiting examples of processing a biofluid sample from a subject to make it suitable for analysis according to the current invention includes removing the cells from the sample, deproteinizing the sample, or homogenizing the tissue to form slurry. Additional examples of tissue processing depend on the biofluid to be analyzed and the biomolecule to be measured. Such embodiments can be envisioned by a person of ordinary skill in the art and are within purview of the current invention.

In one embodiment, the current invention provides a method of measuring concentration of Cortisol in a subject. A suitable biofluid sample can be obtained from the subject to measure Cortisol levels. Non-limiting examples of such biofluid samples include saliva or blood. Concentration of Cortisol in biofluid samples from a subject can be measured to detect the presence of a disease or assessing the likelihood of development of the disease, for example, Addison's disease, Cushing's syndrome, adrenal insufficiencies, psychological stress, or post-traumatic stress disorder. In this embodiment, anti-Cortisol antibodies (anti-$C_{ab}$) can be attached to the sensing electrode surface.

In a further embodiment, the current invention provides a method of measuring concentration of cholesterol in a subject. A suitable biofluid sample can be obtained from the subject to measure the cholesterol concentration. Non-limiting examples of such biofluid samples include blood, serum, or plasma. Concentration of cholesterol in biofluid samples from a subject can be measured to detect the presence of a disease or assessing the likelihood of development of the disease, for example, coronary heart disease, stroke, peripheral vascular disease, diabetes, or high blood pressure. In this embodiment, anti-cholesterol antibodies can be attached to the sensing electrode surface.

In an even further embodiment, the current invention provides a method of measuring a cancer biomarker in a subject, for example, a protein biomarker. A suitable biofluid sample can be obtained from the subject to measure the biomarker level. In this embodiment, antibodies against the protein biomarker can be attached to the sensing electrode surface.

In another embodiment, the current invention provides a method of measuring a hormone to detect the presence or assessing the likelihood of development of the disease associated with an abnormal level of the hormone. A suitable biofluid sample can be obtained from the subject to measure the hormone level. In this embodiment, antibodies against the hormone can be attached to the sensing electrode surface. Examples of diseases associated with abnormal levels of various hormones are well known to a person of ordinary skill in the art and such embodiments are within the purview of the current invention.

In further embodiments of the invention the current invention provides methods of detecting or measuring the levels of biomolecules originating from infectious agents. Suitable biofluids and suitable binding agents can be designed based on the infection and the infectious agent associated with the infection. Accordingly, the current invention can be used to detect infections from bacteria, viruses, protozoa, prions, and fungi. Additional examples of infectious agents are well known to a person of ordinary skill in the art and such embodiments are within the purview of the current invention.

A person of ordinary skill in the art will appreciate that the current invention can be modified in a variety of ways to detect the levels of biomolecules associated with the presence or an increased likelihood of the development of a number of diseases and such embodiments are within the purview of the current invention.

EXAMPLES

Following are examples that illustrate embodiments and procedures for practicing the invention. These examples should not be construed as limiting.

Example 1: An LTCC-Based Microfluidic System for Label-Free, Electrochemical Detection of Cortisol This examples provides a fully automated low temperature co-fired ceramic (LTCC) based electrochemical biosensor platform for the detection of Cortisol. This examples provides the design, fabrication, integration, and testing of the integrated microfluidic system. The electrochemical biosensor consists of IDE Au electrodes, onto which Cortisol antibodies are immobilized using a SAM matrix of DTSP. Finite element based simulation was used to optimize the fluid flow dynamics and washing efficiency required for biosensing in the LTCC microfluidic assay chamber. Cortisol was used as a model analyte to demonstrate electrochemical biosensing in a fully automated microfluidic system. Cortisol was detected in a linear range of 10 pM-100 nM at a sensitivity of 0.207 µA/M using cyclic voltammetry (CV).

System Design

Figure 1B:
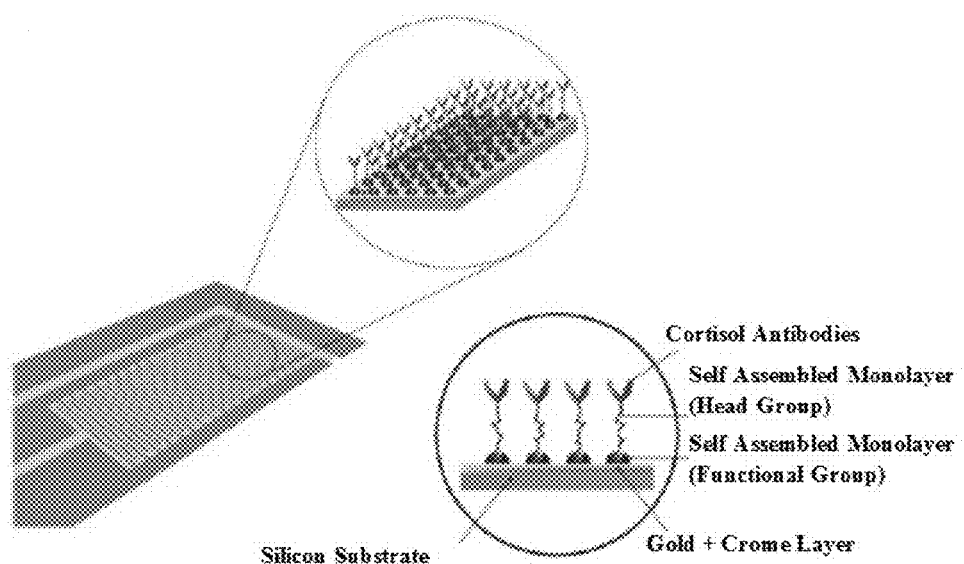

An embodiment of the electrochemical biosensor of the current invention is schematically illustrated in FIG. 1a. In this embodiment, the system consists of two microchannels, a reaction chamber, and a disposable sensing electrode chip that integrates into the LTCC microfluidic manifold. The two microchannels are intended for sample/buffer introduction and waste removal respectively. A three-way solenoid fluidic valve is used to switch the inlet channel between the sample and buffer solution. The reaction chamber provides the space for the incubation of sample on the sensing electrode surface.

The sensing electrode comprises disposable IDE Au electrodes. The interdigitated array consists of about 15 µm wide electrode fingers at a pitch of about 15 µm in an area of about 5 mm×5 mm (FIG. 1b). Anti-$C_{ab}$ are immobilized onto the IDE using a SAM of DTSP as the immobilizing matrix. Electrochemical response is measured using cyclic voltammetry in the presence of a phosphate buffer saline (PBS) solution containing 5 mM ferro-ferri cyanide $[Fe(CN)_6]^{3-/4-}$ as redox species. The binding of Cortisol to the Anti-$C_{ab}$ alters the electron transfer properties at the sensing electrode surface thereby providing an electrochemical response at the sensing electrode surface proportional to the concentration of Cortisol.

CFD (Computational Fluid Dynamics) Simulation

Figures 2A, 2B, 2C:
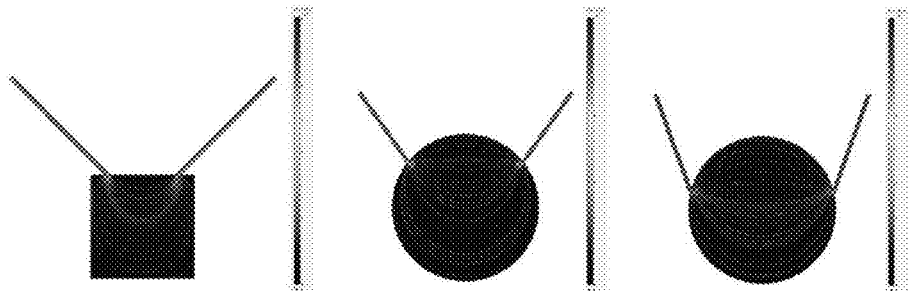
FIGS. 2A-2C. Results of CFD simulation in (a) square chamber; (b) circular chamber and (c) circular chamber with inlet and outlet channels are modified position.

A step in the biosensing assays involves washing the sensing electrode after sample incubation to remove unbound chemicals and other non-specific entities from the sensing electrode surface prior to making electrochemical measurements. Opacity of LTCC material hinders the observation of fluid flow; therefore a computational fluid dynamic (CFD) approach was used to characterize fluid flow profiles to obtain optimum washing efficiency in the assay chamber. All numerical computation presented herein were performed using COMSOL Multiphysics. Simulation was performed for a two-dimensional, incompressible Navier-Stokes flow. A noslip condition was assumed along the walls of the microchannel and physical values of water (dynamic viscosity: 0.89 cP; density: 1000 kg/m$^3$) were used in the numerical computation. The effect of the position of the inlet and outlet microchannels on the flow profile and the geometry of the assay chamber were investigated. A constant flow rate (10 µL/min) was applied across the cross-section of inlet and outlet microchannels. FIG. 2a represents the fluid flow trajectories in a square chamber. In the square chamber, the presence of dead volumes was identified along with the formation of vortices, where washing of the electrode would not be effective. Based on these observations, a design modification was incorporated, where the chamber shape was made circular. While dead volumes were eliminated in the circular chamber, it was observed that the fluid flow trajectory was still unevenly distributed across the chamber area (FIG. 2b). The angles of the inlet and outlet channels were varied and FIG. 2c presents the optimized design where the fluid flow trajectory was observed to be evenly distributed across the circular chamber. Also, the velocity field and pressure were found to be evenly distributed in the circular chamber. The maximum Reynolds number was computed to be ~0.01 confirming laminar flow in the microchannels.

Microfluidic Design

Figure 3A:
Figure 3B:
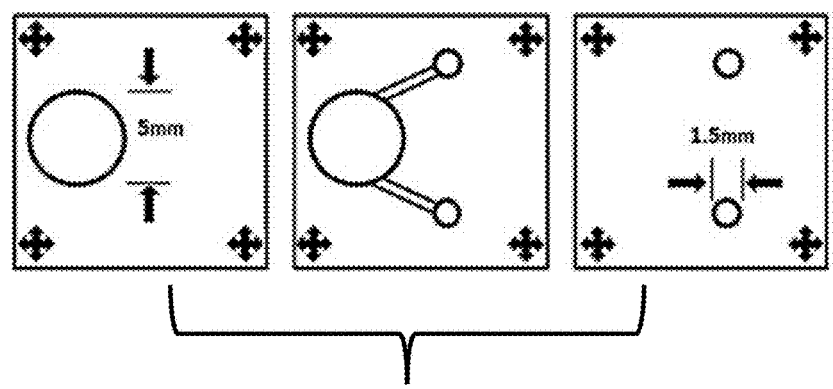

Based on the outcome of the CFD simulation, the optimized design of the electrochemical biosensor is presented in FIG. 3. The cross sectional schematic (FIG. 3a) of the system depicts the assay chamber, microchannels, and the IDE sensing electrode chip. The biosensing electrode chip is designed using three layers of green tape, the design patterns of which are presented in FIG. 3b. The bottom most layer (i) defines the reaction chamber (5 mm diameter) that interfaces with the sensing electrode using a rubber O-ring. The reaction chamber is designed for a volume of 10 µL, therefore will require three layers of the bottom layer to provide the required volume. The middle layer (ii) defines the inlet and outlet microchannels for sample/buffer introduction and waste removal respectively.

The top-most layer (iii) provides the cover to the microchannels and ports for incorporating fluidic connectors. A blowout illustration of the three-layer LTCC microfluidic manifold with the sensing electrode chip is presented in FIG. 3c. The sequence of operation of the system described is as follows.

The sample (10 µL) was introduced into the reaction chamber through the inlet microchannel at a flow rate of 10 µL/min (1 minute) until the chamber is filled with the sample. The sample was then allowed to incubate on the sensing electrodes (static condition) for completion of the immunoreaction.

The detection solution (30 µL of PBS containing 5 mM Fe(CN)$_6^{3-/4-}$) was then introduced into the reaction chamber (10 µL/min for 3 min) to remove the sample from the sensor surface (unbound fraction removal) and to fill the chamber with the detection solution for electrochemical response measurements. After completion of electrochemical measurements, the buffer was aspirated from the chamber (10 µL/min) and the sensor chip was removed and disposed.

To preferentially select the sample and buffer going into the inlet microchannel, a solenoid three-way valve (The Lee Company) was used. The valve maintains a default path where the fluid flows into valves primary inlet ports and exits through a common outlet port (FIG. 4a) and upon activation of the valve, fluid flow switches to a secondary inlet port while exiting through the same common outlet (FIG. 4b). The valve requires a threshold current of 150 mA and 5 V to actuate. FIG. 4c presents the schematic of the electrical circuit used to actuate the solenoid valve. The circuit uses an opto-isolator to separate the grounds within the same circuit. The opto-isolator provides the necessary current to trigger the transistor to a state of saturation; where in the transistor is used as a switch. The circuit provides to the valve 4.87 V and 158 mA, which was found to be sufficient to activate the valve.

Fabrication of LTCC Microfluidic Manifold

For fabrication of the LTCC microfluidic manifold, LTCC green tapes (DuPont 951) were purchased from DuPont. The green tapes were patterned using a computer controller 10.6 µm $CO_2$ laser (Universal Laser Systems) having a spot size of 35 µm. The patterned LTCC layers were sequentially aligned using an aligning fixture that was built in-house (FIG. 5a). The LTCC stack is then laminated using an isostatic hot press (PHI-Tulip) at 150° C. for 15 min at a pressure of 3000 psi. Post-lamination, the LTCC structure was co-fired in an oxygen rich programmable furnace by carefully ramping the temperature up to 850° C. (FIG. 5b). Fluidic connectors made from polydimethylsiloxane (PDMS) (Dow Corning) were attached to the inlet and outlet ports of the microfluidic chip and tygon tubing was used to introduce the fluids from a programmable 2-syringe pump network (New Era Pumps). A two-piece acrylic fixture designed and fabricated in-house was used to integrate the microfluidic manifold with the disposable sensing electrode chip. A rubber O-ring was used to provide a leak-free interface between the sensor chip and the assay chamber.

Fabrication and Functionalization of Sensing Electrode

The interdigitated electrodes were fabricated on an oxidized 4" silicon wafer using conventional microfabrication process. First, the electrode patterns were determined using photolithography. Next, Cr (20 nm) and Au (150 nm) were deposited using an E-beam evaporator.

The microelectrode patterns were finally obtained on the silicon wafer by a liftoff process. For functionalization of the electrode, DTSP and sodium borohydride ($NaBH_4$) were purchased from Thermo Fisher Scientific. Monoclonal Anti-$C_{ab}$ antibody, Cortisol protein, and all other chemicals were purchased from Sigma-Aldrich. PBS (10 mM, pH 7.4) was prepared by dissolving 1 tablet in 200 mL of de-ionized (DI) water and used to prepare the anti-$C_{ab}$ (1 mg/mL) and Cortisol solutions.

Prior to functionalization, the electrodes were immersed in freshly prepared piranha solution to clean the surface. The electrodes were next immersed in 2 mg/mL solution of DTSP in acetone for 2 h for SAM formation. DTSP was reduced using sodium borohydride (10 mg/mL in DI water). The DTSP/Au electrodes were first rinsed with acetone and then by water to remove any unbound DTSP molecules. Anti-$C_{ab}$ (10 µL) was immobilized on to DTSP/Au electrode for 2 h followed by carefully washing with PBS (pH 7.4, 10 mM) to remove any unbound molecules. Anti-$C_{ab}$ binds covalently (amide bond) via a *facile* reaction between amino group of antibody and reactive succinimidyl group of the DTSP-SAM surface. Ethanolamine (EA) (10 µL) was immobilized (10 min) onto anti-$C_{ab}$/DTSP/Au sensing electrode to block unreacted succinimidyl group on DTSP-SAM and later washed with PBS. The fabricated sensing electrodes were stored in refrigerator at 4° C. (dry) when not in use.

CV was utilized to characterize the stepwise fabrication of the sensing electrodes using Autolab Potentiostat/Galvanostat (Eco Chemie, Netherlands) in 10 mL of PBS solution (10 mM, pH 7.4) containing 5 mM $Fe(CN)_6^{3-/4-}$ as a redox probe. CV studies were conducted at a potential range from −0.4 to 0.6 V at 20 mV/s.

Results and Discussion

Microfluidic System

Figure 6B:
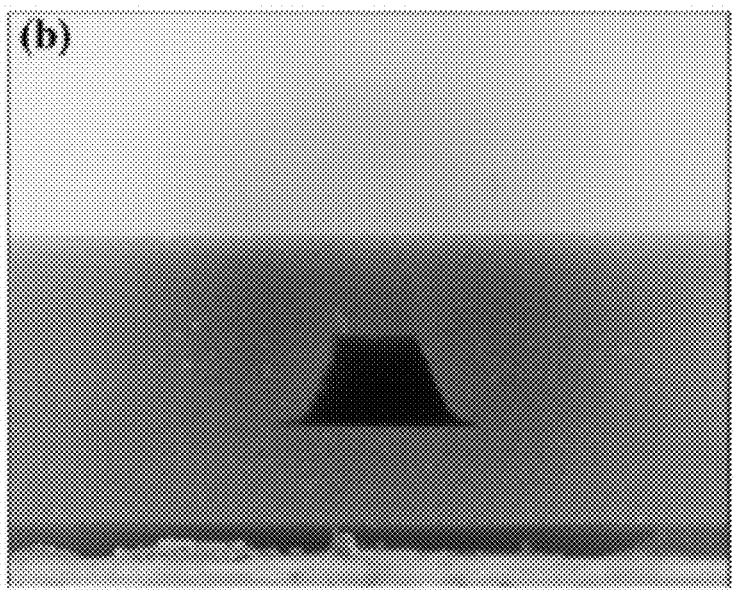
Figure 7A:
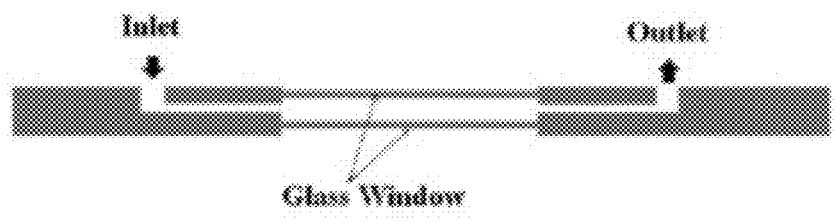
Figure 7B:
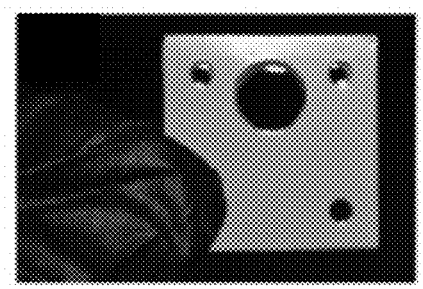

FIG. 6a presents a picture of the fabricated LTCC microfluidic manifold with connectors and tubing attached. During the lamination stage, no sacrificial material was used to fill the channels to prevent channel sagging. Instead, a sequential lamination process, where every layer was sequentially added during the lamination process, was used to obtain sagging and delamination free microchannels. FIG. 6b presents a cross sectional image of the microchannel. The trapezoidal shape of the microchannel cross section is typical of microchannels fabricated using LTCC and results from the excessive burning on only one side of the soft LTCC tapes during laser patterning. The thickness of each individual layer was measured to be 150±5 µm after firing. Due to the trapezoidal cross-section, the width of the channel varied from 100±5 µm at the top to 150±5 µm at the base of the microchannel. For characterizing the fluid flow in the assay chamber, a modified design was utilized, where a glass window was incorporated at the top and bottom of assay chamber to visualize the flow of the fluids entering and exiting the assay chamber. FIG. 7a presents a schematic of the LTCC-glass chip used for fluid flow characterization. Bembnowicz et al. (2010) have previously demonstrated the process of incorporating glass windows into LTCC structures. Microscope glass cover slips were sandwiched between LTCC layers post-lamination. During the co-firing process, between 650 and 750° C., glass softens and bonds to the adjacent LTCC layers, however, the surface tension forces of molten glass assist in maintaining the structure of the glass sheet to accommodate the shrinking of the LTCC structure. Post-sintering clear glass windows were obtained (FIG. 7b) with no signs of cracking or distortion. To observe the trajectory of fluid flow and to determine the washing efficiency, red color dye solution was used to simulate the sample (contrast) and DI water was used to simulate the washing buffer.

In FIG. 7c is presented the snapshots of fluid flow in the microfluidic assay chamber. FIG. 7c(i)-c(v) presents the introduction of the sample into the assay chamber and FIG. 7c(vi)-c(x), the washing of the chamber is demonstrated. It can be observed that the trajectory of fluid flow is in accordance with the results obtained from the simulation (FIG. 2c). Also, the designed flow rate (10 µL/min) and volume (30 µL) of the buffer provided the required washing efficiency. Similarly, the functioning of the fluidic valve was also characterized using two contrast dyes and the functioning of the fluidic valve was verified and is presented in FIG. 8. In this three-way valve, the common outlet is in the center with each of the two inlets on either side. Under normal conditions (FIG. 8a), the left input (blue) is open, and the actuation of the valve (FIG. 8b) switches the flow to the right input (red). A two-piece acrylic fixture designed to house the microfluidic system was fabricated in-house. FIG. 8c presents the picture of the testing fixture with the microfluidic chip, the fluid control valve and the disposable sensor chip.

Electrochemical Biosensor

Figure 9A:
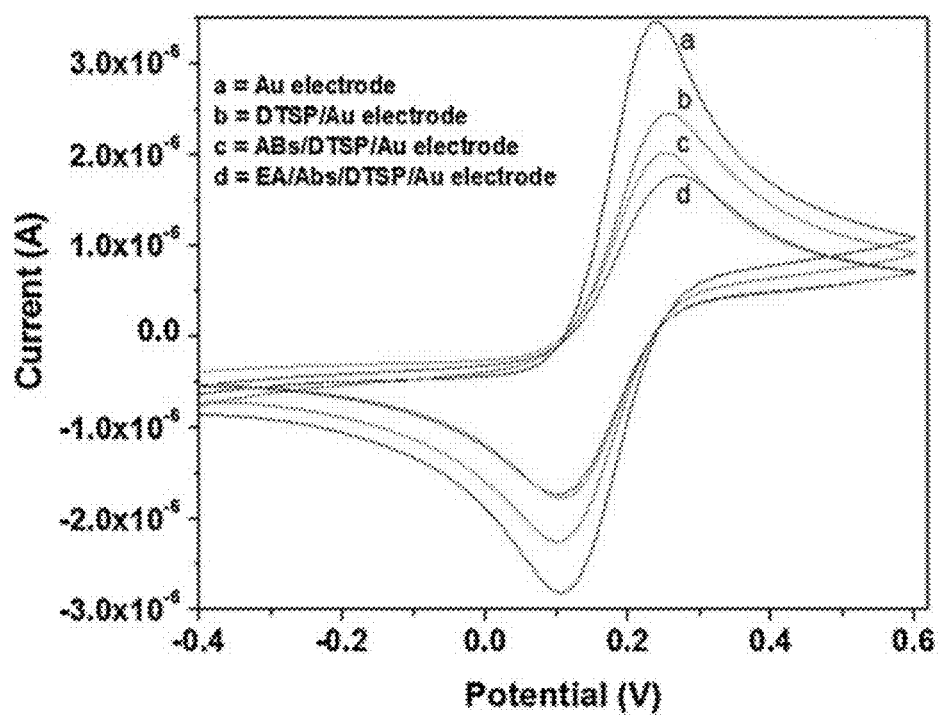
FIGS. 9A-9B. (a) The CV curves on the Au electrode (curve a), DTSP/Au electrode (curve b), anti-$C_{ab}$/DTSP/Au sensing electrode (curve c), and EA/anti-$C_{ab}$/DTSP/Au sensing electrode (curve d) carried out in PBS [50 mM, pH 7.4 containing 5 mM [Fe(CN)$_6$]$^{3-/4-}$]; (b) calibration curve obtained from the electrochemical response studies of EA/anti-$C_{ab}$/DTSP/Au-Mac sensing electrode as a function of Cortisol concentration (10 pM-100 nM).

The electrochemical behavior of the stepwise fabrication of sensing electrode was studied using CV. The CV curves on the bare Au electrode (curve a), DTSP/Au electrode (curve b), anti-$C_{ab}$/DTSP/Au bioelectrode (curve c), and EA/anti-$C_{ab}$/DTSP/Au bioelectrode (curve d) were carried out in PBS (50 mM, pH 7.4 containing 5 mM [Fe(CN)$_6$]$^{3-/4-}$) as shown in FIG. 9a. The Au electrode showed very well-defined oxidation and reduction behavior of redox moieties Fe(II)/Fe(III) in the electrolyte. The magnitude of electrochemical response current of the Au electrode was found to decrease after the deposition of DTSP-SAM (curve b). This suggests the formation of DTSP-SAM, and due to the insulating nature of DTSP-SAM, electron transfer from the medium to electrode is hindered. After the immobilization of anti-$C_{ab}$ onto the DTSP/Au electrode, the magnitude of the electrochemical response current further decreased (curve c). This suggests that successful binding of anti-$C_{ab}$ with DTSP immobilizing matrix further hinders the electrons transport from medium to electrode. Furthermore, the magnitude of current response decreases after the immobilization of EA onto the anti-$C_{ab}$/DTSP/Au-Mac (curve d) biosensing electrode due to blocking of non-specific binding sites of anti-$C_{ab}$ that insulate the electrode and perturb electron propagation.

CV studies have also been carried out to optimize the pH (data not shown) of PBS solution for electrochemical measurements. The magnitude of current response is pH dependent and maximum current response is observed at pH 7.4. Thus, PBS of pH 7.4 has been used for electrochemical studies, which is the recommended pH to get the antigen-antibody complexes of high biological activity. The electrochemical response of EA/anti-$C_{ab}$/DTSP/Au sensing electrode has been studied as a function of Cortisol concentration (10 pM-100 nM) using CV technique under identical experimental conditions (PBS (10 mM, pH 7.4) containing 5 mM [Fe(CN)$_6$]$^{3-/4-}$ as a redox probe and potential ranging from −0.6 V to +0.6 V).

Incubation time for the binding of anti-$C_{ab}$ with Cortisol was determined using CV studies, since the magnitude of response current is dependent on electron transfer kinetics. The results of CV studies reveal that the magnitude of current response decreases over time due to the increased binding between anti-$C_{ab}$ and Cortisol causing electron transfer resistance. However, no further decrease in current was observed after 30 min indicating optimum incubation time. Hence, during the electrochemical sensing measurement the sensing electrode was incubated in each Cortisol concentration for 30 min.

Figure 9B:
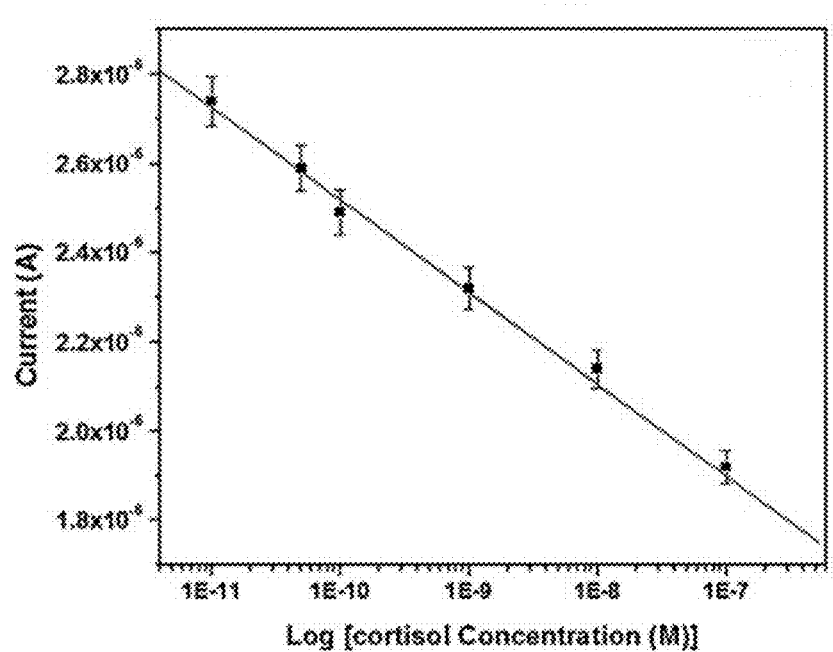

The electrochemical response studies were conducted in triplet set and the average value was used for analysis. The magnitude of response current decreased with increasing Cortisol concentrations (10 pM-100 nM) using a standard successive addition technique. This is due to the formation of immuno complexes between Anti-$C_{ab}$ and Cortisol resulting in electron charge transfer hindrance at the electrode electrolyte interface. The magnitude of electrochemical response current of EA/Anti-$C_{ab}$/DTSP/Au sensing electrode is linearly dependent to the logarithm of Cortisol concentration (FIG. 9b) and obeys the relation:

$$Y = A(4.4 \times 10^{-5}) - 0.207 \times 10^{-6} \times \log(\text{Cortisol concentration}); R = 0.997.$$

The EA/anti-$C_{ab}$/DTSP/Au sensing electrode exhibits linear range from 10 pM to 100 nM, at a detection limit of 10 pg/mL and sensitivity of 0.207 µA/M with a correlation coefficient of 0.997 (SD: 0.78 nA). The value of the association constant (Kα) was estimated at $9 \times 10^{11}$ L/mol indicating strong affinity of anti-$C_{ab}$ with Cortisol, attributed to the immobilization of anti-$C_{ab}$ onto the DTSP/Au electrode in the desired orientation. The EA/anti-$C_{ab}$/DTSP/Au sensing electrode showed a minimum change from baseline value (~3-5%) with respects to PSA (100 pg/mL), EGFR (100 pg/mL), NSE (100 pg/mL) as interferents. However, a significant change (FIG. 9a) was obtained with Cortisol confirming that the sensing electrode is not affected by the interferents.

The above described embodiment of the current invention provides a fully automated LTCC based electrochemical biosensor for electrochemical detection of Cortisol. Using CFD, a 3D microfluidic architecture was designed and optimized to ensure efficient sample introduction and subsequent washing of the sensing electrodes during the biosensing regime. The fabrication process of the LTCC based microfluidic system is detailed and its advantages such as simplicity, low-cost, and rapid fabrication process are demonstrated. The biosensing platform was successfully integrated into the LTCC based microfluidic system for detection of Cortisol. The integrated biosensor demonstrates a linear range of 10 pM to 100 nM at a sensitivity of 0.207 μA/M in an automated and controlled microfluidic environment. The successful integration of the biosensor with the microfluidic manifold presents the potential application of LTCC based microfluidic systems for antibody based detection of various other biomarkers.

Example 2: Electrochemical Biosensing of Saliva Cortisol

The detection of Cortisol in saliva is an important screening tool for psychological stress and health monitoring, including the diagnosis of Cushing's syndrome, Addison's disease, and post-traumatic stress disorder (PTSD). Cortisol is a steroid hormone produced as part of the body's stress response, and is secreted by the hypothalamic-pituitary-adrenal (HPA) system. Cortisol is often called the "stress hormone", but it also plays an important role in the homeostasis of physiological processes e.g., adrenal, immune, circulatory, metabolic, etc. Thus role of Cortisol in these anomalies is important. Moreover, Cortisol abnormalities are often a good indicator of chronic conditions such as Addison's disease, Cushing's syndrome, and adrenal insufficiencies. Recently, there have been reports that correlate Cortisol variations to important applied phenomena, such as increased stress among farmworkers and correlation with farmworkers being exposed to insecticides and pesticides.

Although Cortisol detection is important diagnostic tool, the state-of the art in Cortisol detection is mostly limited to laboratory based techniques such as chromatography, RIA, ECLIA, ELISA, SPR, QCM etc. In these techniques, the turn-around time from sampling to results is typically from days to a few weeks, and often involves sending samples to a diagnostic laboratory. This embodiment of the current invention provides Cortisol sensing platforms that can be deployed at POC in order to get instantaneous results of Cortisol values in biofluids.

The Cortisol concentration in saliva is lower than total serum Cortisol by a factor of 10, and the correlation between serum and salivary markers is strong. Salivary Cortisol concentrations accurately reflect the serum concentration at various times of day (morning, evening, and around midnight). Moreover, the salivary Cortisol contains only free Cortisol making protocol easier.

This embodiment of the current invention provides a simple, inexpensive, and label-free electrochemical biosensing platform for highly sensitive and selective detection of Cortisol in saliva. The electrochemical biosensor was successfully tested on multiple specimen samples of saliva collected at different time intervals from two participants. The Cortisol concentrations obtained from the electrochemical biosensor correlated with those obtained using ELISA.

The electrochemical biosensor of the current invention was used to measure Cortisol concentrations in saliva samples of farm workers. IDEs functionalized with DTSP-SAM followed by covalent immobilization of Anti-$C_{ab}$ were used to detect the concentration of Cortisol present in the saliva samples. The results obtained from the electrochemical detection were validated through ELISA protocol currently in use. As such, this embodiment provides a Cortisol sensing protocol using saliva samples collected from human subjects and its validation with the standard ELISA technique.

Saliva Sample Collection

Saliva samples were derived from two female agricultural workers of reproductive age who engaged in shift-work. Much evidence indicates that Cortisol levels vary significantly among female shift workers, and that stress associated with agricultural work is associated with Cortisol level variation, as is exposure to Cortisol. Farmworkers were 24 and 39 years old and were recruited based on the following criteria: be at least 18 years of age, and work in agricultural fieldwork, work early morning shifts, and have exposure to pesticides. These samples were drawn from another study measuring the effects of a behavioral study to assess pesticide exposures and stress response.

Samples were collected at awakening, before their first work break, at their lunch break (before eating), upon arrival from work, and before bedtime. Samples were stored by participants' at freezing (−20° C.) until they were transferred by the project team and stored at −80° C. in a field lab. The standard protocol requires saliva samples to be stored at −20° C. or lower for preservation of natural and biological properties over extended periods and while transportation. Saliva samples were collected by each farmworker using a Salivette (Sarstedt Inc., Rommelsdorf, Germany), which consists of a small cotton roll inside a centrifuge tube. Each farmworker took the Salivette home after receiving written and oral instruction on how to collect saliva. Participants collected a saliva sample by chewing on the cotton roll for 60 seconds.

The collected saliva samples were stored at −20° C. to maintain its biological characteristics. Before testing, the saliva samples were thawed to room temperature and centrifuged at 3500 rpm for 15 min to extract saliva from salivettes. The separated saliva was then pipetted out and kept at −20° C. These samples were used to detect Cortisol using electrochemical biosensors and ELISA.

Biosensor Fabrication

Electrochemical Cleaning of IDEs

Figure 10A:
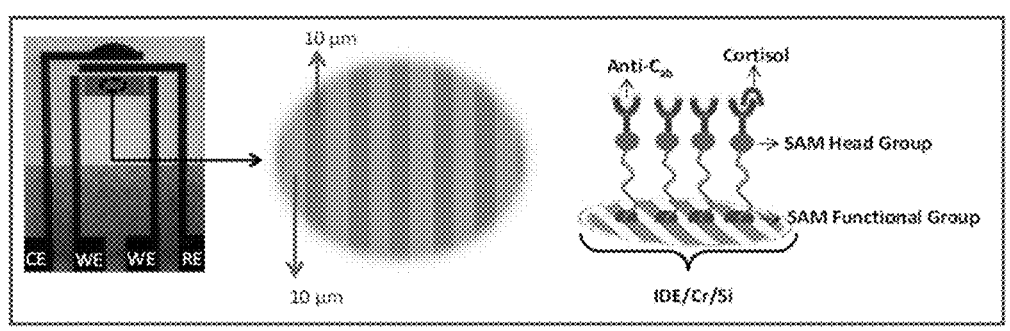
FIGS. 10A-10B. A) Schematic presentation of IDEs and fabrication of biosensor. B) Proposed electrochemical and immunochemical reaction on the surface of IDEs. During immunological reaction, the binding of Cortisol with Anti-$C_{ab}$ block the electron transport generated from medium [Fe(II) to Fe(III) conversion] to IDE. This results in reduced current from the oxidation and reduction cycles, which can be correlated to the concentration of the Cortisol molecules bind onto sensing electrode surface.
Figure 11A:
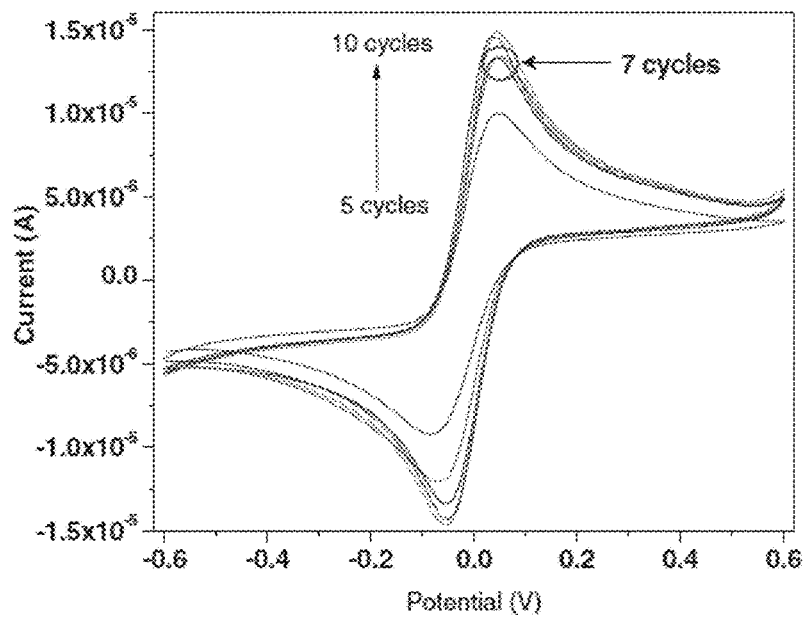
FIGS. 11A-11B. CV studies of electrochemically cleaned (0.1 M $H_2SO_4$) IDEs at different scanning cycles (A), CVstudies of 9 IDEs (electrochemically cleaned, 7 cycles (B) using 5 μL PBS (pH 7.4) containing 5 mM [Fe(CV)$_6$]$^{3-/4-}$ redox moieties at 50 mV/s.
Figure 11B:
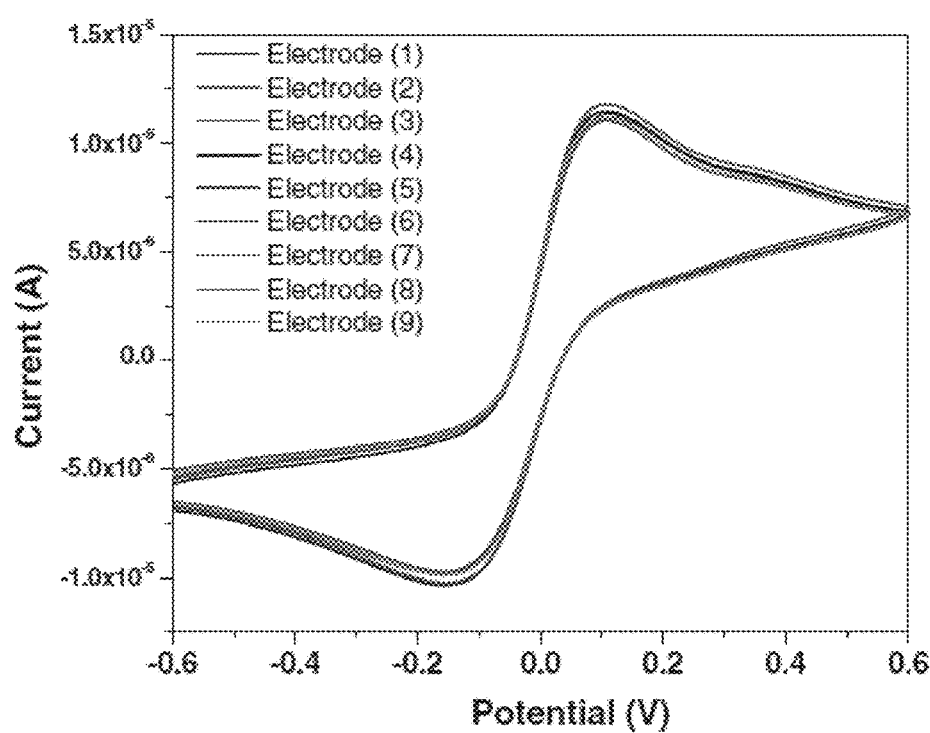

IDEs (chamber volume ~5 μL, electrode width and electrode gap 10 μm) were procured from Micrux Technologies (FIG. 10A). The IDEs were electrochemically cleaned prior to DTSP-SAM modification through performing cyclic voltammetry [CV, Autolab potentiostat/galvanostat (Eco Chemie, Netherlands)] using 5 μL of 0.1 M $H_2SO_4$ as a function of varying scanning cycles at scan rate of 50 mV/S. The parameters of the IDE cleaning process were optimized using CV techniques in 5 μL PBS (pH 7.4) containing 5 mM $K_4[Fe(CN)_6]^{3-/4-}$ at scan rate of 50 mV/s (FIG. 11A). The magnitude of current response obtained was found to increase with increasing cleaning scanning cycles. Higher current response was observed in case of IDEs cleaned using 9 cycles and higher. However, the electrode started to etch after scanning cycles. Thus IDEs were cleaned using 7 scanning cycles in 5 μL, 0.1 M $H_2SO_4$. All IDEs were cleaned using same process and exhibited identical current response (within ~2% variation, FIG. 11B) without morphological damage.

Fabrication of DTSP-SAM onto IDEs and Electrochemical Cortisol Biosensing

DTSP, $NaBH_4$, Anti-$C_{ab}$, Cortisol, and all other chemicals were purchased from Sigma-Aldrich and were used without any further purification. For fabrication of DTSP-SAM, the IDEs were immersed in 2 mg/mL solution of DTSP in acetone for 2 h. During the SAM fabrication, DTSP was reduced using $NaBH_4$ (10 mg/mL in DI water). After SAM modification, all DTSP/IDEs were rinsed with acetone and then by DI water to remove unbound DTSP particles. Anti-$C_{ab}$ (5 μL) was covalently immobilized via a *facile* reaction between amino group of antibody and reactive succinimidyl group of the DTSP SAM surface. The DTSP-SAM/IDE were incubated with anti-$C_{ab}$ for 2 hrs followed by carefully washing with PBS (pH 7.4, 10 mM) to remove any unbound molecules. PBS solution (10 mM, pH 7.4) was prepared by dissolving 1 PBS tablet in 200 mL of DI water and used to prepare the anti-$C_{ab}$ (1 mg/mL) and Cortisol solutions. The non-binding sites of Anti-$C_{ab}$/DTSP/IDEs on the sensing electrodes were blocked using 5 μL of ethanolamine (EA). The incubation time was 10 min. EA/Anti-$C_{ab}$/DTSP/IDEs were washed with PBS and stored in refrigerator at 4° C. when not in use. The fabrication of SAM onto IDEs and biosensor development is shown in FIG. 10A.

Measurement of Cortisol

Figure 10B:
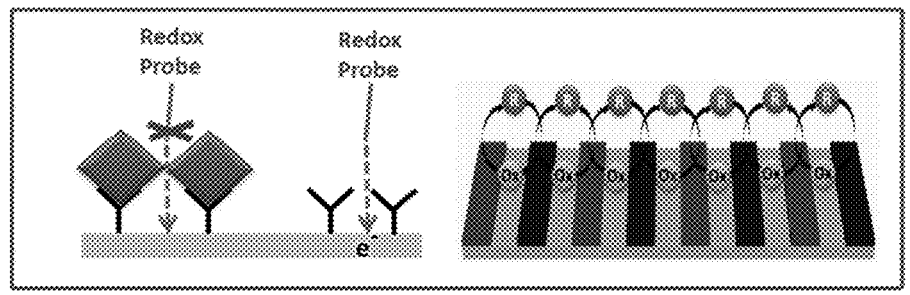

The fabricated EA/Anti-$C_{ab}$/DTSP-SAM/IDEs sensing electrodes were used to detect various concentration of Cortisol using CV techniques in 5 μL PBS (pH 7.4) containing 5 mM $[Fe(CN)_6]^{3-/4-}$ as redox species. pH of 7.4 was chosen for electrochemical response studies of the sensing electrode, as this is the recommended pH for biomolecules to presume higher biological activity (Introduction to antibodies, 2nd Edition by Chemicon International). The electrochemical and biosensing reaction on IDEs surface is shown FIG. 10B. The fabricated sensing electrodes were used to detect Cortisol in saliva samples of two specimens collected at different time intervals. 5 μL of saliva sample was placed on the electrochemical biosensor. The saliva sample was incubated for 30 minutes on the sensing electrodes to ensure proper binding. Sensing electrodes were then washed for about 10 minutes using PBS to remove unbound and non-specifically bound saliva components.

Cortisol ELISA kit was obtained from Arbor assays, MI, and standard protocol was adopted to detect saliva Cortisol. Briefly, 40 μl of 4× diluted saliva was used to detect Cortisol.

Results and Discussion

Figure 12:
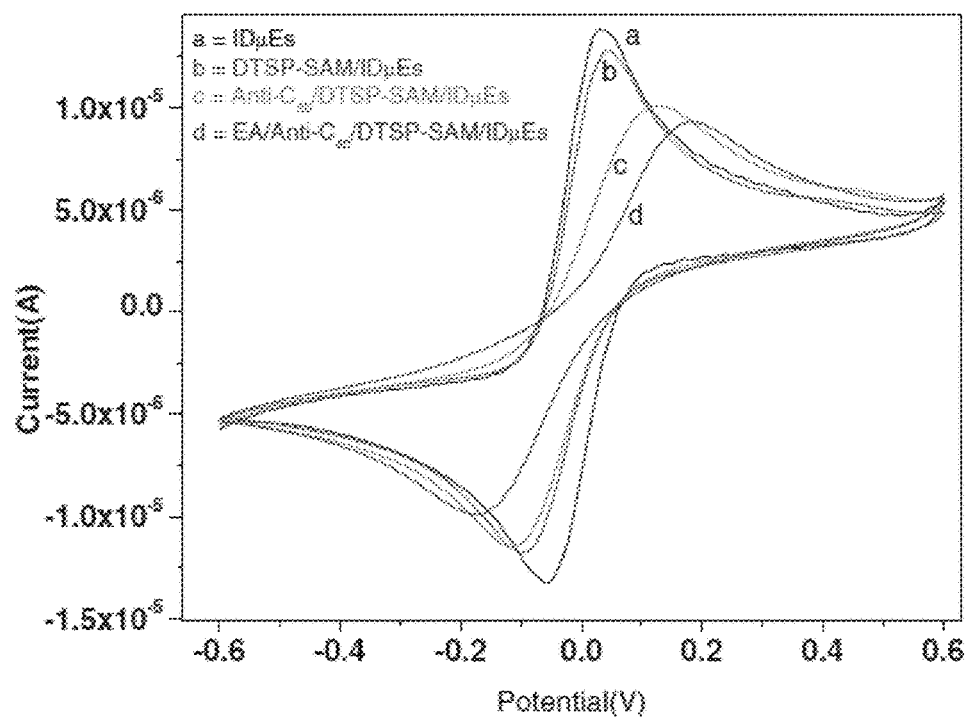
FIG. 12. A) CV studies of IDEs (a) DTSP-SAM modified IDEs (b), Anti-$C_{ab}$ immobilized DTSP-SAM/IDE sensing electrode (c), and EA-immobilized anti-$C_{ab}$ DTSP-SAM/IDE sensing electrode (d), using 5 ml PBS containing 5 mM Fe(CV)$_6$]$^{3-/4-}$ at 50 mV/s.

Electrochemical Characterization:

CV technique was used to optimize the electrochemical biosensor which is utilized to detect Cortisol. FIG. 12 shows the results of the CV studies for IDEs (a), DTSP-SAM/IDEs (b), Anti-$C_{ab}$/DTSP-SAM/IDEs biosensing electrode (c) and EA/Anti-$C_{ab}$/DTSP-SAM/IDEs (d) in 5 μL PBS (pH 7.4) containing 5 mM Fe(II)/Fe(III) at 50 mV/s in a potential range from −0.6 to 0.6V. CV of IDEs exhibited a well-defined oxidation and reduction peaks of redox moieties present in the electrolyte. It can be seen that the magnitude of electrochemical current response decreases after modifying IDEs by DTSP-SAM. This suggests that SAM hinders the electron transport from Fe(II)/Fe(III) to IDEs due to successful thiol bonding between DTSP-SAM and Au of IDEs which indicates successful DTSP-SAM fabrication. After the immobilization of Anti-$C_{ab}$ the magnitude of current from DTSP-SAM/IDEs further decreases due to the covalent binding between Anti-$C_{ab}$ and DTSP via amide bond formation. The magnitude of current from EA-Anti-$C_{ab}$/DTSP-SAM/IDEs sensing electrode was lower than Anti-$C_{ab}$/DTSP-SAM/IDEs sensing electrode. This reduction of current is a clear indication that the non-conducting EA blocks the non-binding sites on the sensing electrode and reduce the electron transport from electrolyte to IDEs.

The CV studies of electrodes and sensing electrodes have been performed as a function of scan rate (10-100 mV/s). A linear relationship between magnitude of oxidation/reduction current and square root of scan rate (data not shown) has been observed for all electrodes. This confirms that the assay is a linear-diffusion-driven process. It obeys Randles-Sevcik equation:

$ip = (2.69 \times 10^5) n^{2/3} ACD^{1/2} v^{1/2}$, where n is the number of transferred electrons, A is the active area of electrode, C is the bulk concentration of the redox species, D is the diffusion coefficient and v is the scan rate.

The magnitude of current response is also linearly related to differences in potentials revealing the *facile* electron transport from electrode to IDE surface.

Electrochemical Response Studies of Cortisol

Figure 13A:
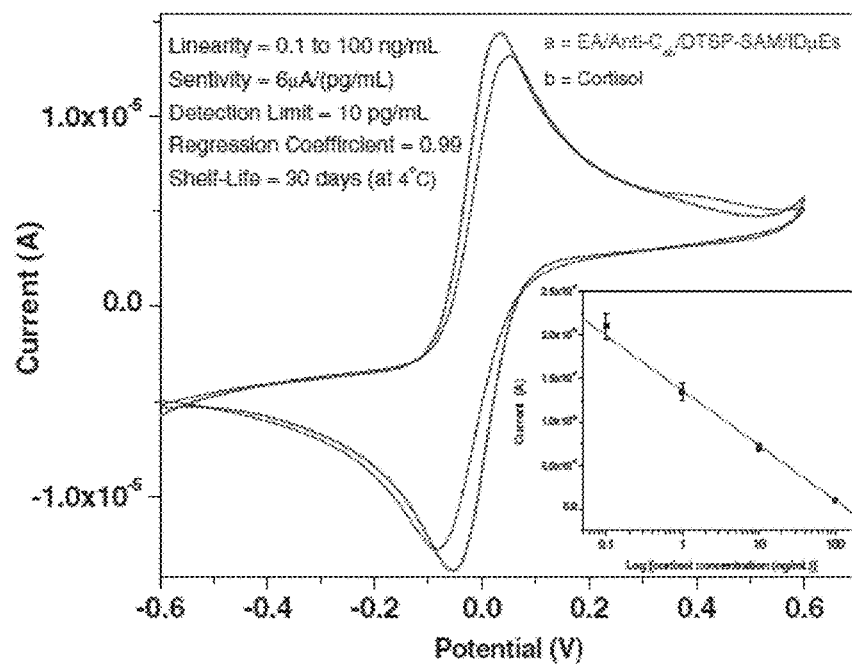
FIGS. 13A-13B. A) Electrochemical response of EA/Anti-$C_{ab}$/DTSP-SAM/IDEs sensing electrode after addition of standard Cortisol solution, Inset; Calibration curve plotted between the magnitudes of current response obtained and logarithm of Cortisol concentration (10 pg/mL to 100 ng/mL), B) Study of interferents effect, PSA (100 pg/mL), NSE (100 pg/mL), EGFR (100 pg/mL) and BSA+ Cortisol (100 pg/mL) with respect to Cortisol (100 pg/mL).

Electrochemical response studies of developed DTSP-SAM modified IDEs biosensor as a function of Cortisol concentration (10 pg/mL to 100 ng/mL) was performed using CV technique in 5 μL PBS (pH 7.4) containing 5 mM $[Fe(CN)_6]^{3-/4-}$ with a potential range of −0.6 to 0.6 V at a scan rate of 0.5 mV/s. Prior to electrochemical measurement, 5 μL of each Cortisol sample was incubated on the sensing electrode surface for 30 mins for complete binding of Anti-$C_{ab}$ with standard Cortisol solution. A washing step using 30 μL of PBS was performed to remove the unbound Cortisol from the sensor surface. All the CV measurements were performed in triplets. The result of CV studies indicated that the magnitude of current response decreases on addition of Cortisol (FIG. 13A) due to the formation of insulating complexes between Anti-$C_{ab}$ and Cortisol which further inhibited the electron transport from electrolyte to IDEs surface. A calibration curve (Inset, FIG. 13A) plotted between the magnitude of current response and logarithm of Cortisol concentration was found to be linearly dependent and follow the equation:

$$[Y = 1.5 \times 10^{-5} + 6 \times 10^{-6} \log(\text{Cortisol concentration}); R = 0.99].$$

Figure 13B:
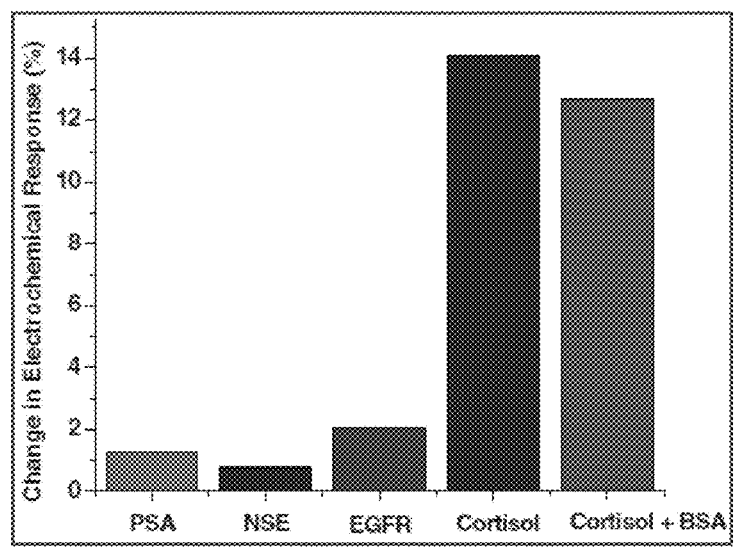

The fabricated EA/Anti-Cab/DTSP-SAM/IDEs sensing electrode exhibited a linearity in the range of 0.1 to 100 ng/mL, a detection limit of 10 pg/mL, a sensitivity of 6 μA/(pg/mL) with the regression coefficient of 0.99 and standard deviation of 0.6 μA. The confirmation of Anti-$C_{ab}$ onto DTSP-SAM/IDEs electrode and its affinity with Cortisol was understood through the association constant (Kα, $3 \times 10^{12}$ L/mol) between Anti-$C_{ab}$ and Cortisol, calculated using Lineweaver-Burke-like plot. Kα value greater than $10^{11}$ is accepted as a demonstration of high affinity. FIG. 13B shows the results of the CV studies of EA/Anti-$C_{ab}$/DTSP-SAM/IDEs sensing electrodes with respects to interferents such as PSA (100 pg/mL), NSE (100 pg/mL), EGFR (100 pg/mL) and BSA+Cortisol (100 pg/mL) with respect to Cortisol (100 pg/mL). The interferents were dispensed on the sensing electrode (EA/Anti-$C_{ab}$/DTSP-SAM/IDEs) and their electrochemical response was measured. The change in electrochemical response of the interferents was compared to that of the sensing electrode and it was found to be of the order of 1-2%. As compared to the change in the response of Cortisol signal, which was in the order of 13-14%, the effects of interferents can be neglected. This demonstrates that the effect of interferents on EA/Anti-$C_{ab}$/DTSP-SAM/IDEs sensing electrode is minimal and the antibodies are selective to the Cortisol molecule. A CV study was also carried out to study the shelf life of the EA/Anti-$C_{ab}$/DTSP- SAM/IDEs sensing electrodes at intervals of 1 week (data not shown). The results of the study showed electrodes were stable for 28 days and beyond that time the electrochemical response reduced.

Electrochemical Biosensing of Saliva Cortisol.

Figure 14A:
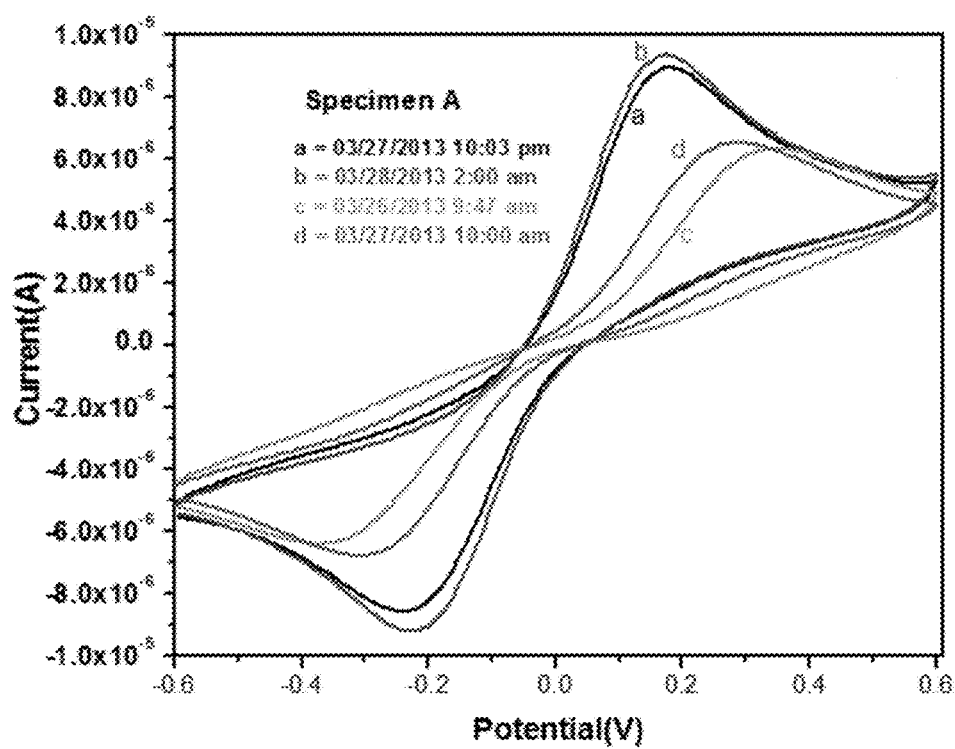
FIGS. 14A-14B. Electrochemical response studies of EA/Anti-$C_{ab}$/DTSPSAM/IDEs sensing electrode as a function of saliva Cortisol of specimen A & B using CV in 5 μL PBS (pH 7.4) containing 5 mM [Fe(CV)$_6$]$^{3-/4-}$ redox moieties at 50 mV/s.
Figure 14B:
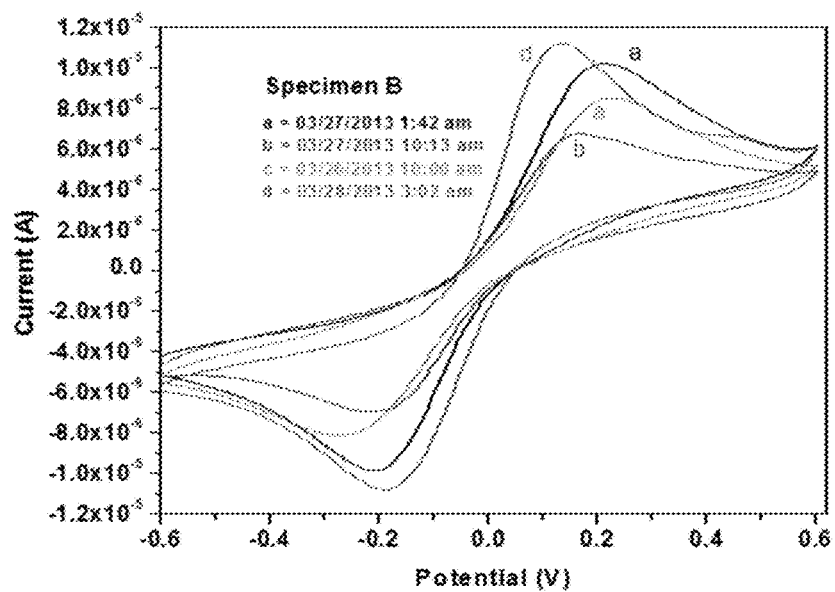

The IDEs based electrochemical biosensor for Cortisol sensing was utilized for testing of Cortisol concentrations in saliva samples. To perform the electrochemical detection, 5 µL of the saliva sample was incubated on the electrochemical biosensor for a period of 30 mins. A washing step using 30 µL of PBS was performed to remove the saliva components and any unbound Cortisol from the sensor surface. FIG. 14 shows the electrochemical response studies of EA/Anti-$C_{ab}$/DTSP-SAM/IDEs sensing electrodes were carried out using CV in 5 µL of PBS containing 5 mM Fe(II)/Fe(III) as the redox probe at scan rate of 50 mV/s. A significant change in current response of biosensing electrode is observed on adding each saliva samples. Cortisol concentration was read using the calibration curve developed in electrochemical response studies. All samples were measured in triplicates and the average was calculated as shown in Table 1. These values were used to validate the values obtained with ELISA technique (shown in Table 2).

TABLE 1

Cortisol values measured in saliva samples using the electrochemical biosensor.

| Specimen | Saliva collection (Time and Date) | Measured electrochemical response (mA) | Cortisol Concentration (Obtained Concentration × 2.2) (nMol/L) | Final Cortisol Concentration (ng/dL) |
|---|---|---|---|---|
| A | Mar. 26, 2013 (9:47 AM) | 7.16 | 3.63 | 131.78 |
|   | Mar. 27, 2013 (10:00 AM) | 7.38 | 3.81 | 138.37 |
|   | Mar. 27, 2013 (10:03 PM) | 12.23 | 0.90 | 32.94 |
|   | Mar. 28, 2013 (2:00 AM) | 8.89 | 1.818 | 65.89 |
| B | Mar. 26, 2013 (10:13 AM) | 5.24 | 9.09 | 329.45 |
|   | Mar. 27, 2013 (1:42 AM) | 7.76 | 2.727 | 98.83 |
|   | Mar. 27, 2013 (10:13 AM) | 4.26 | 14.54 | 428.29 |
|   | Mar. 28, 2013 (3:02 AM) | 9.17 | 1.93 | 69.18 |

TABLE 2

Cortisol values measured in saliva samples using Cortisol ELISA kit.

| Specimen | Saliva collection (Time and Date) | Measured Response (4 × dilution) (% B/Bo) | Cortisol Concentration (pg/mL) 4 × dilution | Final Cortisol Concentration (ng/dL) |
|---|---|---|---|---|
| A | Mar. 26, 2013 (9:47 AM) | 64.133 | 389 | 155.6 |
|   | Mar. 27, 2013 (10:00 AM) | 66.909 | 360 | 144 |
|   | Mar. 27, 2013 (10:03 PM) | 56.113 | 594 | 237.6 |
|   | Mar. 28, 2013 (2:00 AM) | 81.758 | 182 | 72.8 |
| B | Mar. 26, 2013 (10:13 AM) | 41.705 | 995 | 398 |
|   | Mar. 27, 2013 (1:42 AM) | 99.759 | 125 | 50 |
|   | Mar. 27, 2013 (10:13 AM) | 40.956 | 1187 | 474.8 |
|   | Mar. 28, 2013 (3:02 AM) | 96.695 | 87 | 34.8 |

Detection of Salivary Cortisol Using ELISA.

Figure 15:
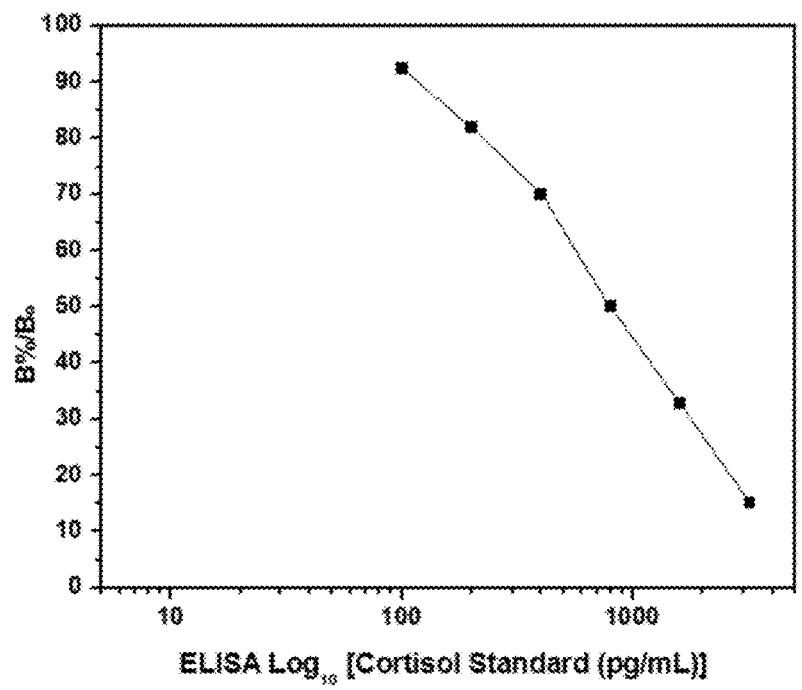
FIG. 15. A calibration curve obtained for determination of the Cortisol concentrations in saliva samples using ELISA.

To validate the results obtained from the electrochemical biosensor, saliva samples from the same salivette were tested for Cortisol using ELISA (Arbor Assays, MI). The protocol prescribed by the ELISA kit vendor was followed for Cortisol detection in saliva samples. To establish the calibration curve for Cortisol measurement, the assay was performed in a 96-well titer plate consisting of six known standard Cortisol concentrations (100, 200, 400, 800, 1600 and 3200 pg/mL) and the saliva samples. The calibration curve obtained from the measurement of the standard solutions is presented in FIG. 15. Next, the saliva samples were diluted 1:4 in the provided assay buffer and 50 µL of saliva samples were utilized for each measurement. Saliva samples from each of the salivettes were tested in triplicate sets and the average value was utilized to determine the final Cortisol concentration and is presented in Table 2.

Figure 16A:
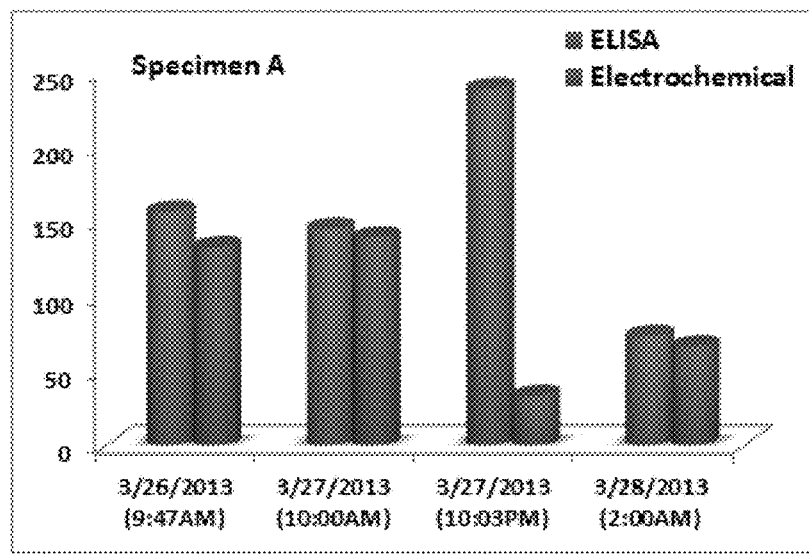
FIGS. 16A-16B. Comparison of Cortisol values obtained by ELISA and the electrochemical biosensor of the current invention.
Figure 16B:
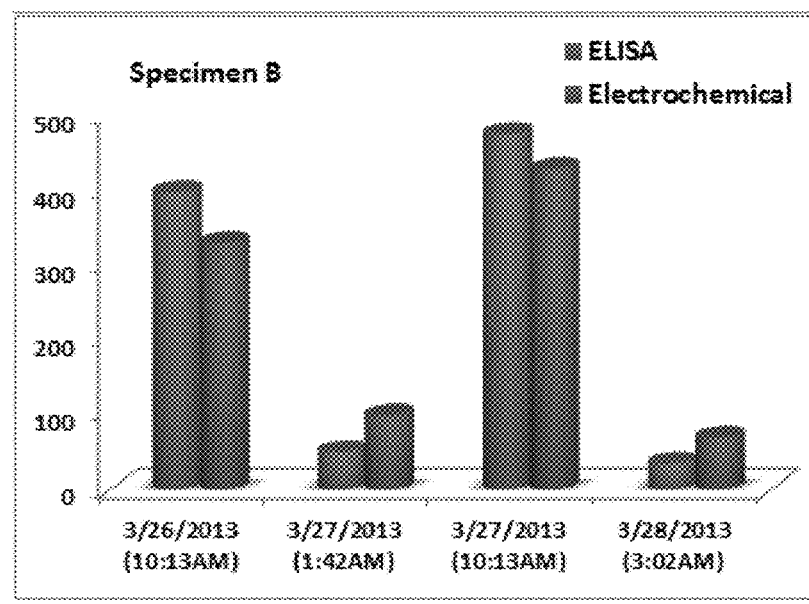
Figure 17A:
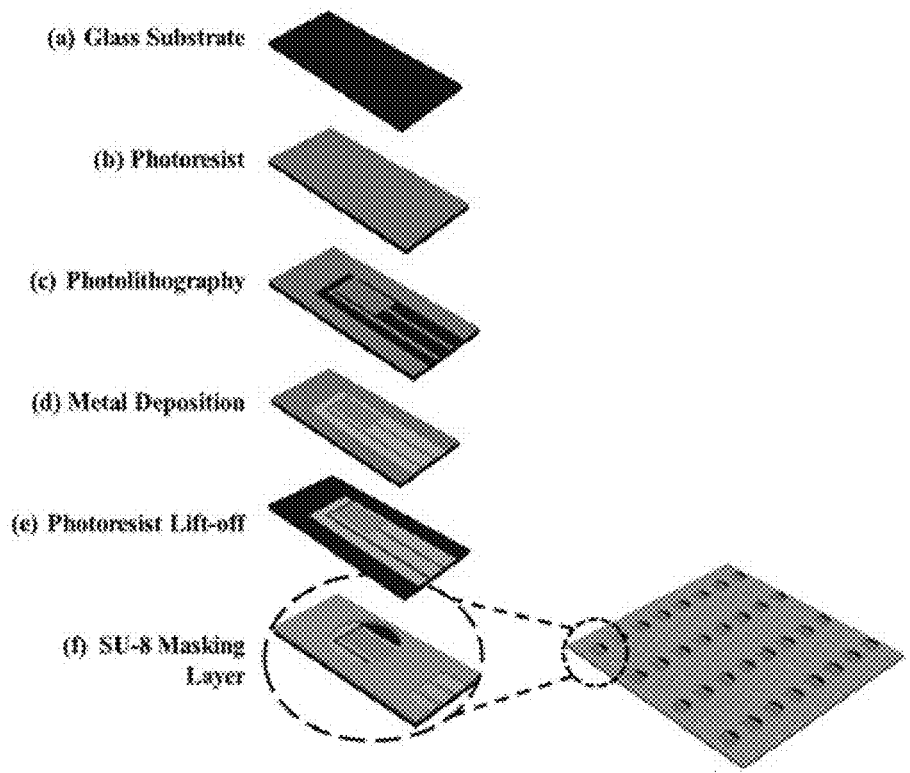
FIGS. 17A-17B. Example of the biosensing electrode architecture.
Figure 17B:
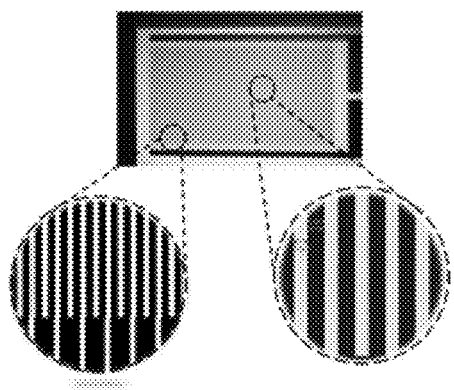
Figure 18:
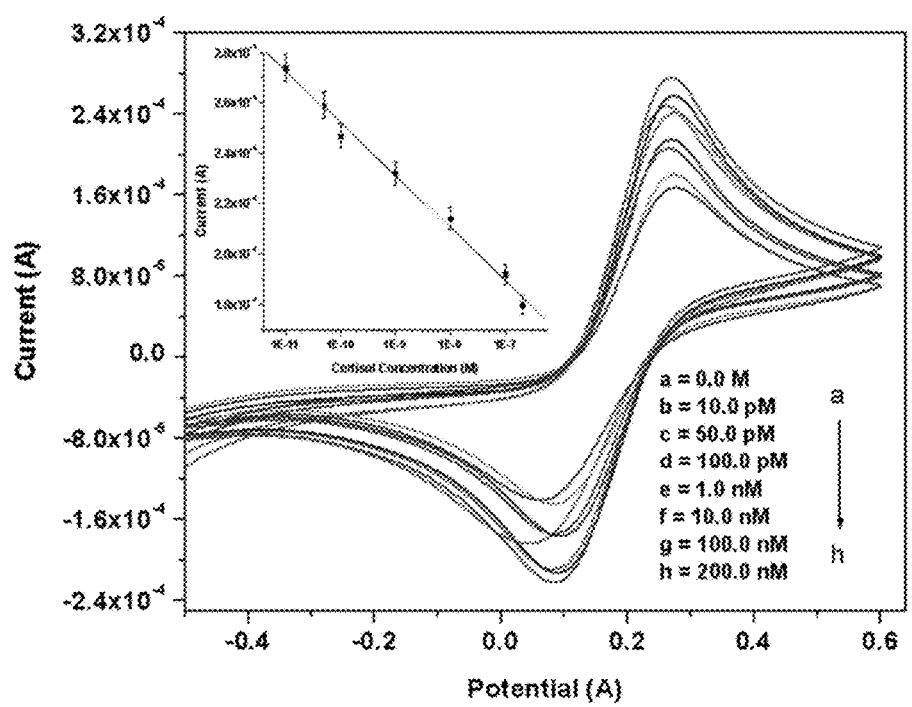
FIG. 18. Graph showing the results of the measurements of Cortisol concentration from 10 pM to 200 nM using CV.
Figure 19A:
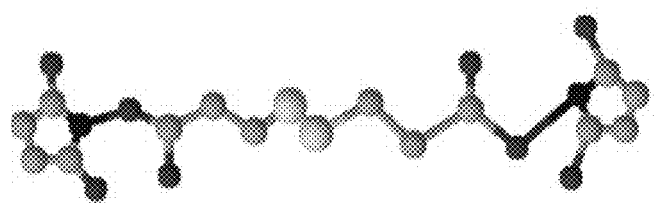
FIGS. 19A-19B. DTSP-SAM fabrication chemistry.
Figure 19B:
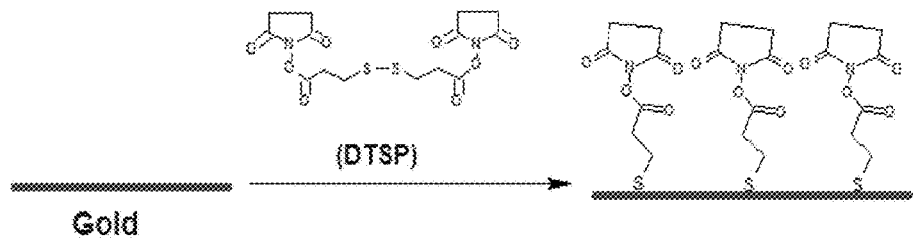
Figure 20:
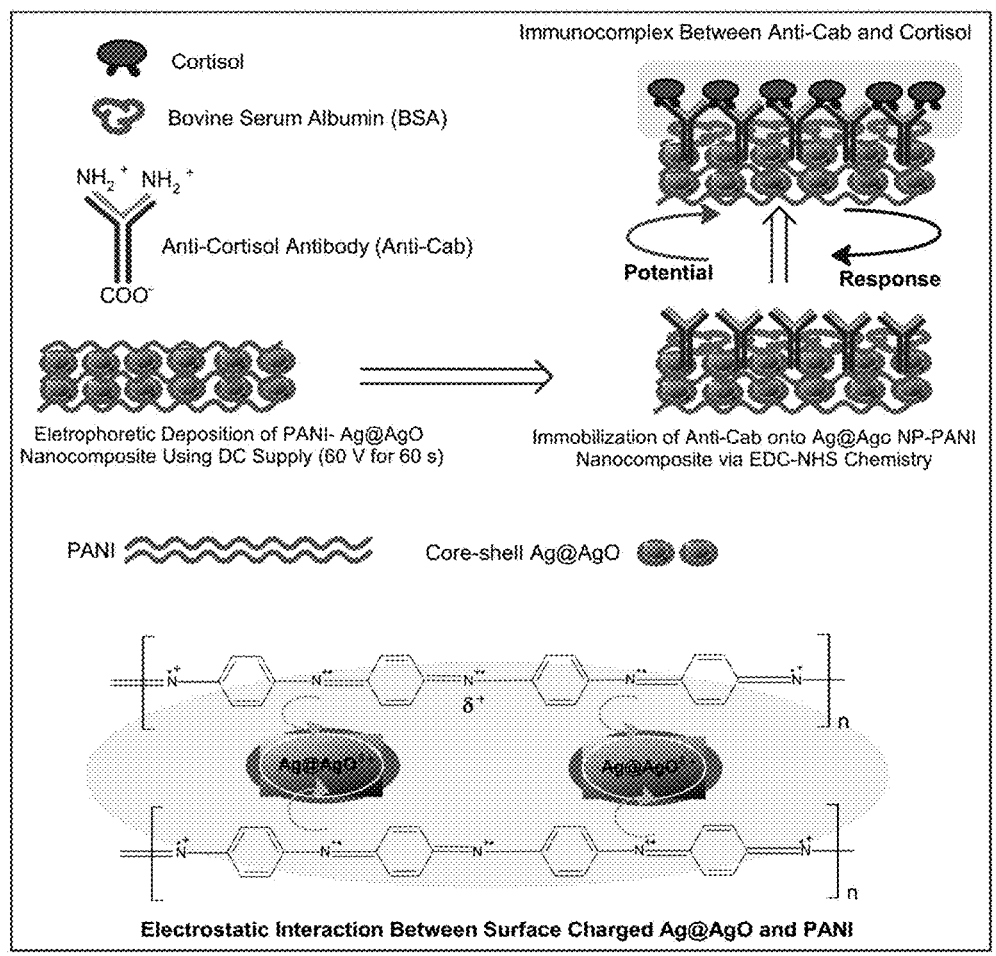
FIG. 20. Schematic of nanocomposite based electrochemical biosensor using polyaniline (PANI) and core-shell Ag@AgO nanoparticles and EDC-NHS chemistry.
Figure 21:
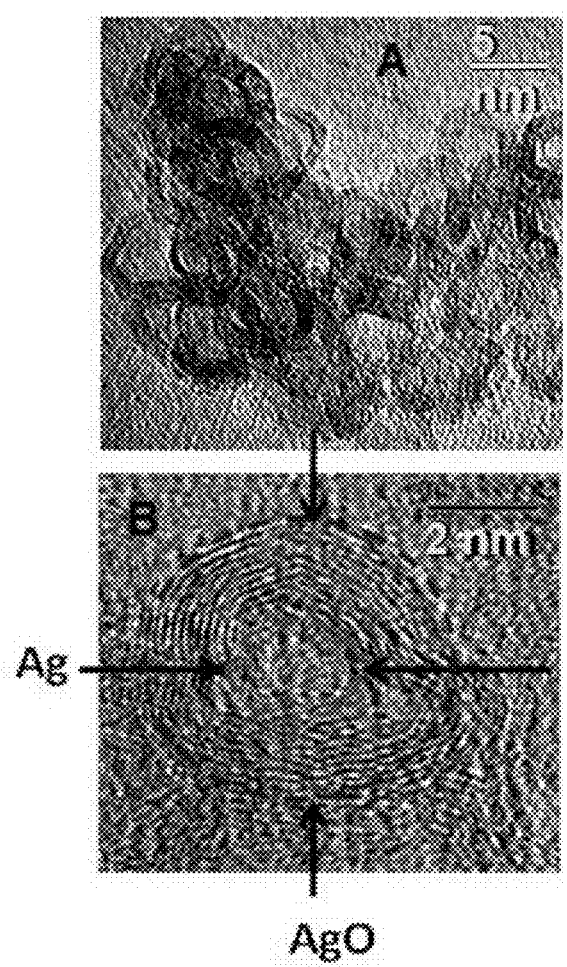
FIG. 21. Transmission Electron Micrograph of Ag@AgO nanocomposite.
Figure 22A:
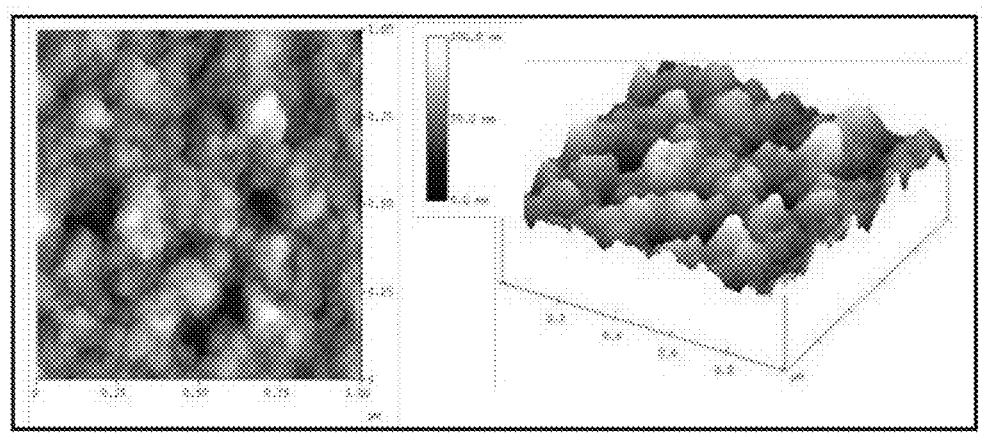
FIGS. 22A-22C. Atomic Force Microscope image of nanocomposite and sensing electrode.
Figure 22B:
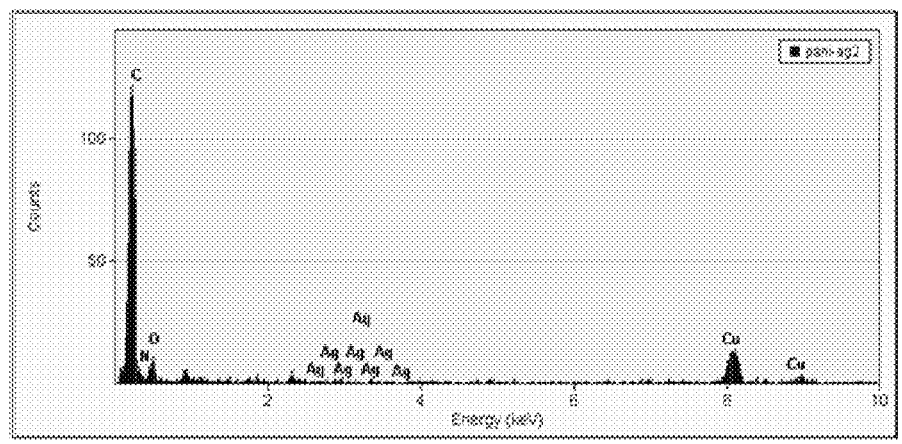
Figure 22C:
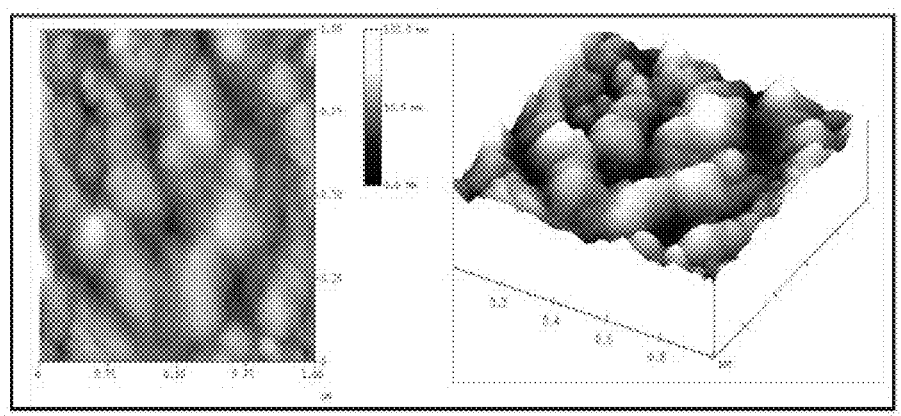
Figures 23, 24:
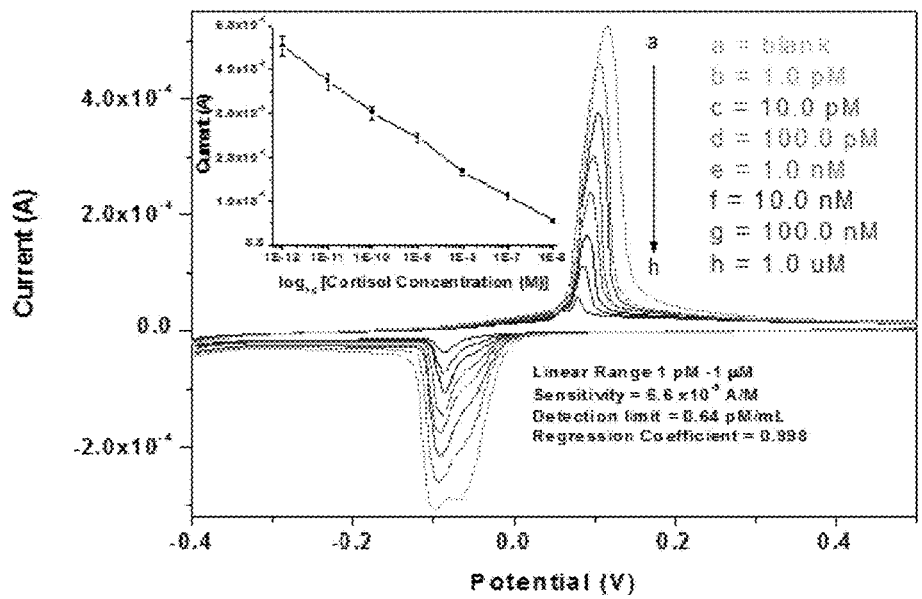
FIG. 23. Graph showing the results of the measurements of Cortisol concentration from 1 pM to 1 μM using CV and the Ag@AgO nanocomposite based electrochemical biosensor of the current invention.
FIG. 24. Comparison of sensing parameters between DTSP-SAM and Ag@AgO-PANI fabricated sensing electrodes.
Figure 25:
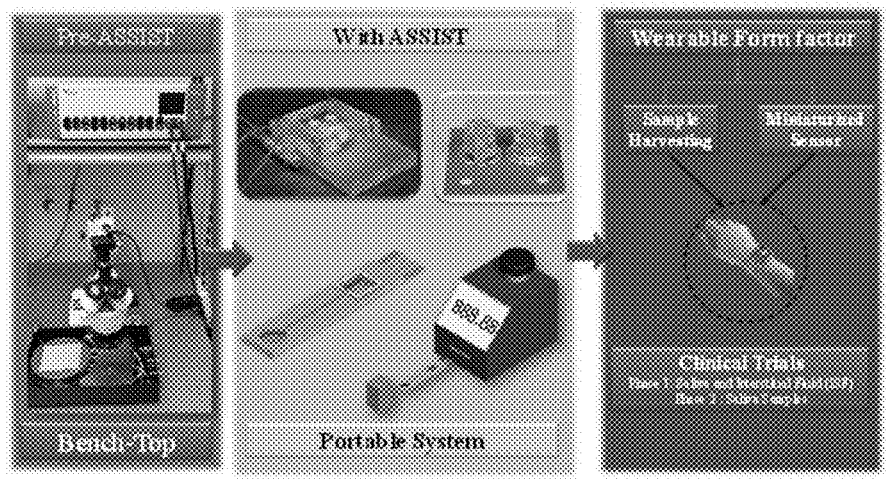
FIG. 25. Evolution of electrochemical biosensor of the current invention from benchtop format to point of care devices.
Figure 26:
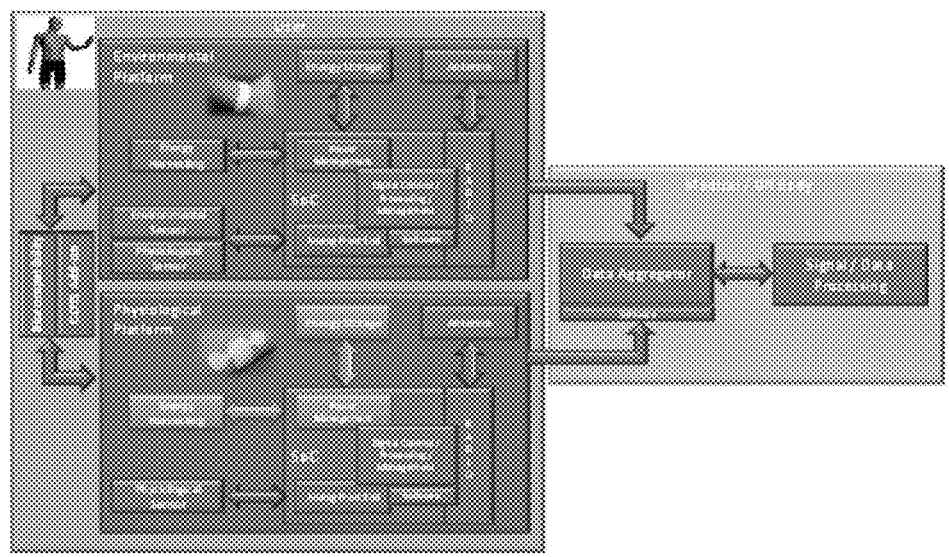
FIG. 26. The electrochemical biosensor of the current invention in an example of a point of care operation.
Figure 27:
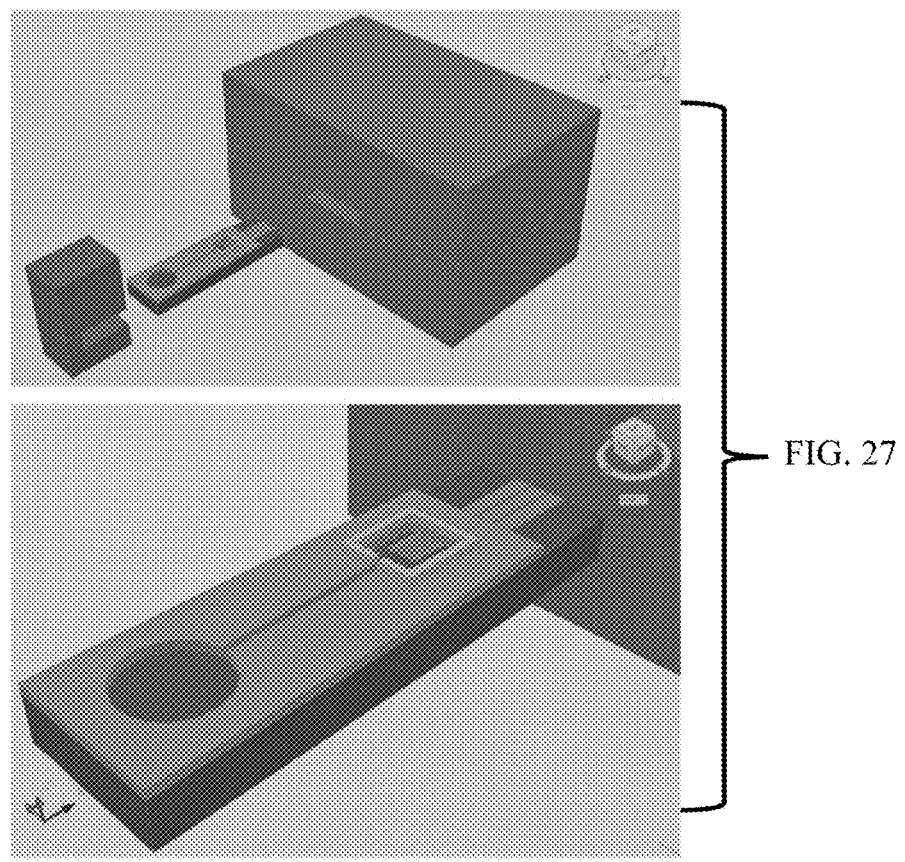
FIGS. 27-31. Various design aspects of the biochemical sensor of the current invention.
Figure 28:
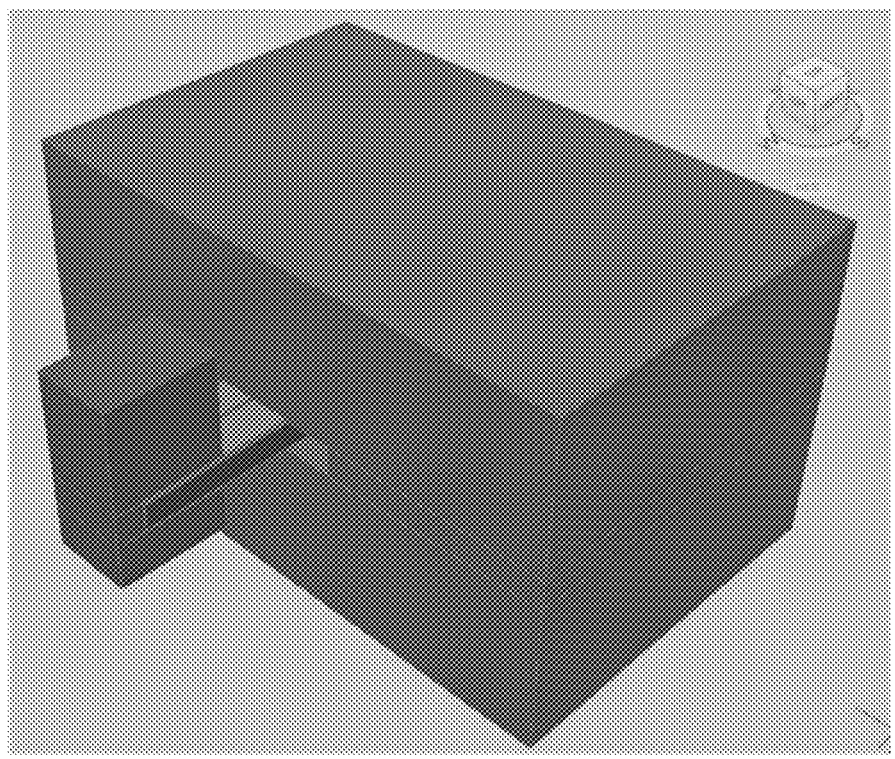
Figure 29:
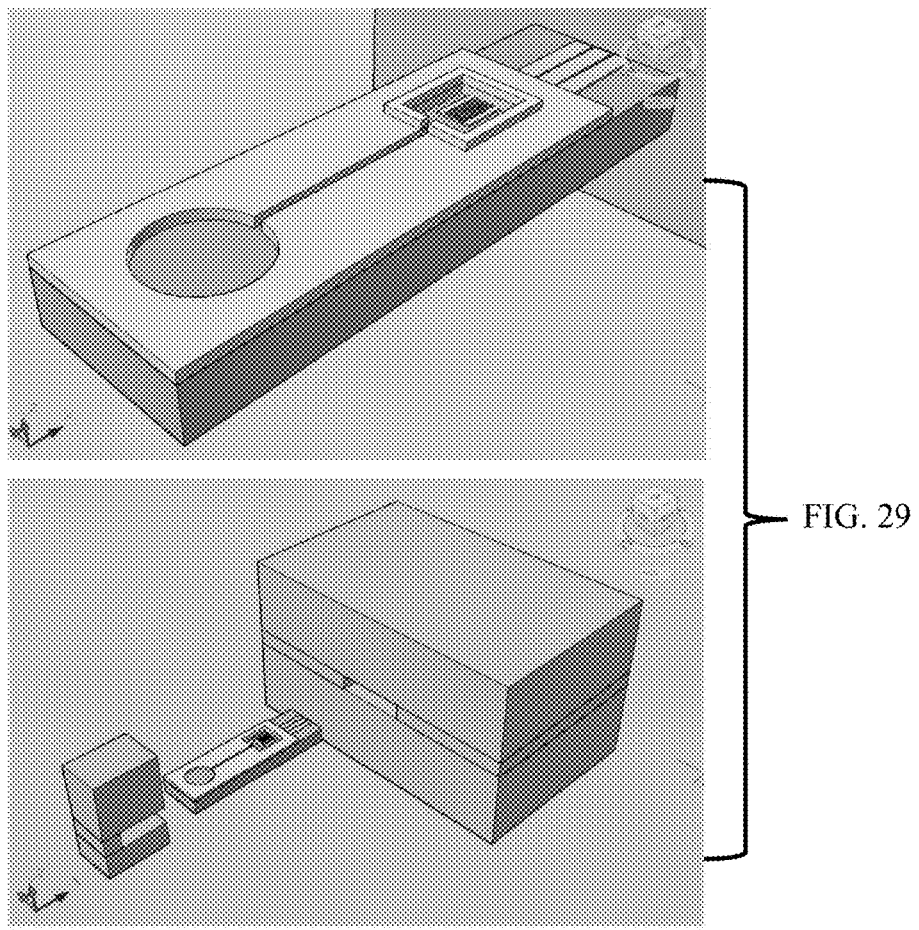
Figure 30:
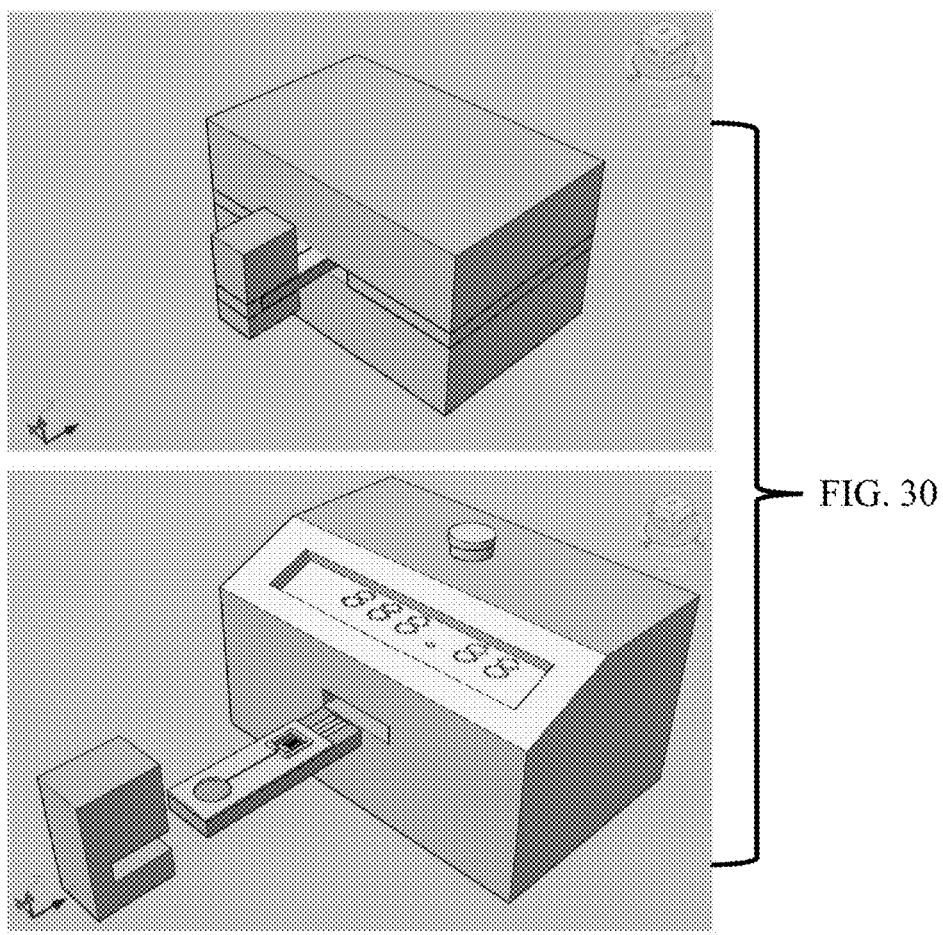
Figure 31:
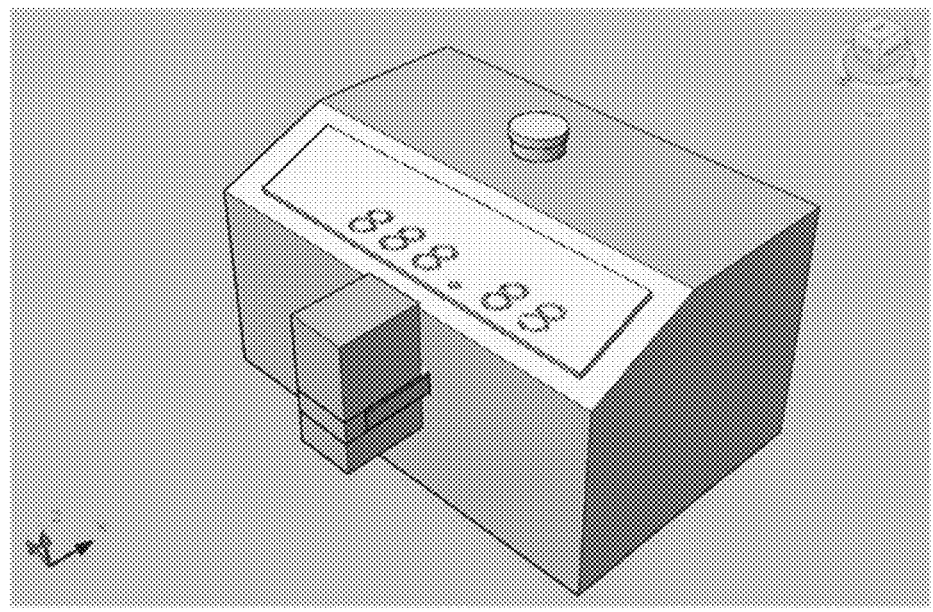
Figure 32:
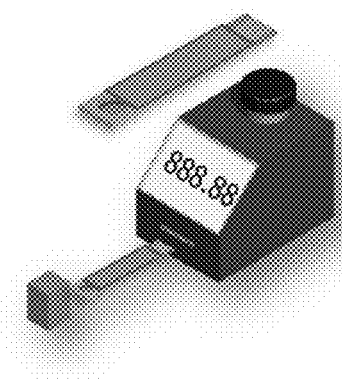
FIG. 32. Miniaturized electrochemical biosensor of the current invention for Cortisol detection.

FIG. 16 shows the comparison of results obtained for Cortisol detection in saliva samples using the electrochemical biosensor and ELISA. The trend observed for the electrochemical measurements were mostly consistent with that obtained from ELISA, except for the saliva sample from Specimen A [Mar. 27, 2013 (10:03 pm)], in which the ELISA value was observed to be a high value at night time. This observed difference may be due to an experimental error of denatured saliva sample. Since both methods have different transduction techniques to detect Cortisol concentration, the outcome were in different magnitudes.

In order to compare and correlate these responses, one had to be scaled to the other. All values of Cortisol concentration obtained from the corresponding electrochemical calibration curve were adjusted by a factor of 2.2 in order to compare them with values obtained using ELISA assays. A good correlation was achieved between the two sets of data, thus enabling quantitative validation of the electrochemical biosensing of Cortisol in a biofluid such as saliva.

CONCLUSION

Electrochemical biosensor of the current invention was utilized for a low-cost and label-free detection of Cortisol via covalent immobilization of Anti-$C_{ab}$ onto DTSP-SAM modified IDEs (chamber volume 5 µL, electrode width 10 µm and electrode gap 10 µm). The fabricated electrochemical biosensor exhibited a detection range from 10 pg/mL to 100 ng/mL, a detection limit of 10 pg/mL, and a sensitivity of 6 µA/(pg/mL) with the regression coefficient of 0.99. The sensor has been used for salivary Cortisol detection in clinically relevant samples and sensing performance has successfully validated using conventional ELISA method. The Cortisol value in saliva samples of two specimens collected at different time intervals using DSTP-SAM/IDEs correlates (within 2-5%) with those obtained using ELISA. The developed sensor is able to reliably detect Cortisol in saliva within physiological range which can be used as marker to understand various physical, behavioral and psychological variables which may affect the central nervous system.

Example 3: The Low Cost Miniaturised Potentiastat for Cortisol Detection

In an embodiment of the invention, the biochemical biosensor for Cortisol detection is miniaturized (Figure and comprises:

1. A miniaturized Micro-Potentiostat (LMP9100), reconfigured to read the electrochemical response from the sensor assay.

2. A microcontroller—BeagleBone™ microcontroller used in this system is a low cost device and was used to send signals that control the microfluidic valves and the miniaturized potentiostat. It interfaces with the microfluidic valves to supply the right amount of sample and buffer solutions to the assay through the microfluidic channels. It interfaces with the potentiostat chip to provide voltage and read the response current and store the values for comparison and data analyses. The microcontroller also interfaces with a display to give out the readings obtained after the measurements.

3. Microfluidic Hub—The microfluidic system consists of the storage chambers for the cortisol sample and the buffer solution. The sample and the Buffer are introduced onto the detector strip sequentially through the microfluidic channels with the help of the fluidic valve that controls the flow of the solution to the test assay.

4. The biosensor assay—It is a three electrode system consisting of the interdigitated working and counter electrodes and a reference/pseudo-reference electrode. The antibodies are immobilized on these electrodes with the help of a self-assembled monolayer of DTSP. Cortisol molecules in the sample are allowed to flow on the electrode strip and bind to anti-$C_{ab}$ antibodies. Current voltammetry measurements are done on the strip and the results are displayed via the microcontroller.

5. The biosensor works by measuring the oxidation and reduction current observed when a sweeping potential is applied to the sensor assay. The alternating voltage applied, causes oxidation and reduction between the working and counter electrode. The electrode interacts with the ions present in the electrolyte and provides a current that corresponds to the oxidation and reduction states of the ions in the sensor assay. The presence of Cortisol Molecules on the Anti-$C_{ab}$ immobilized on the electrodes, block the conduction pathways of the electrons to the underlying electrodes and results in reduced current from the oxidation and reduction cycles, this reduction in the redox current is correlated to the concentration of the Cortisol molecules present on the surface of the sensing electrode.

Example 4: Electrochemical Biosensor of the Current Invention Containing Single Domain Antibodies Preparation of Single Domain Antibodies:

Single domain antibodies specific to an antigen are obtained from organisms of Camelid family by inoculating them against a specific antigen and later separating out the single domain antibody (sdAB). The sdAB used for our biosensors would be purchased from vendors who specialize in extraction and purification of such antibodies.

Electrochemical measurements IDE was used as a substrate to immobilize the sdAB specific to the antigen. The sdAb immobilised electrode was dipped in PBS (pH 7.4) containing 5 mM [Fe $(CN)_6$]$^{3-/4-}$ as redox species. The CV curves were obtained for antibody coated biosensor. These curves were compared to the CV curves obtained after dispensing the sample to be measured on the sdAB immobilised biosensing electrode.

Figure 33:
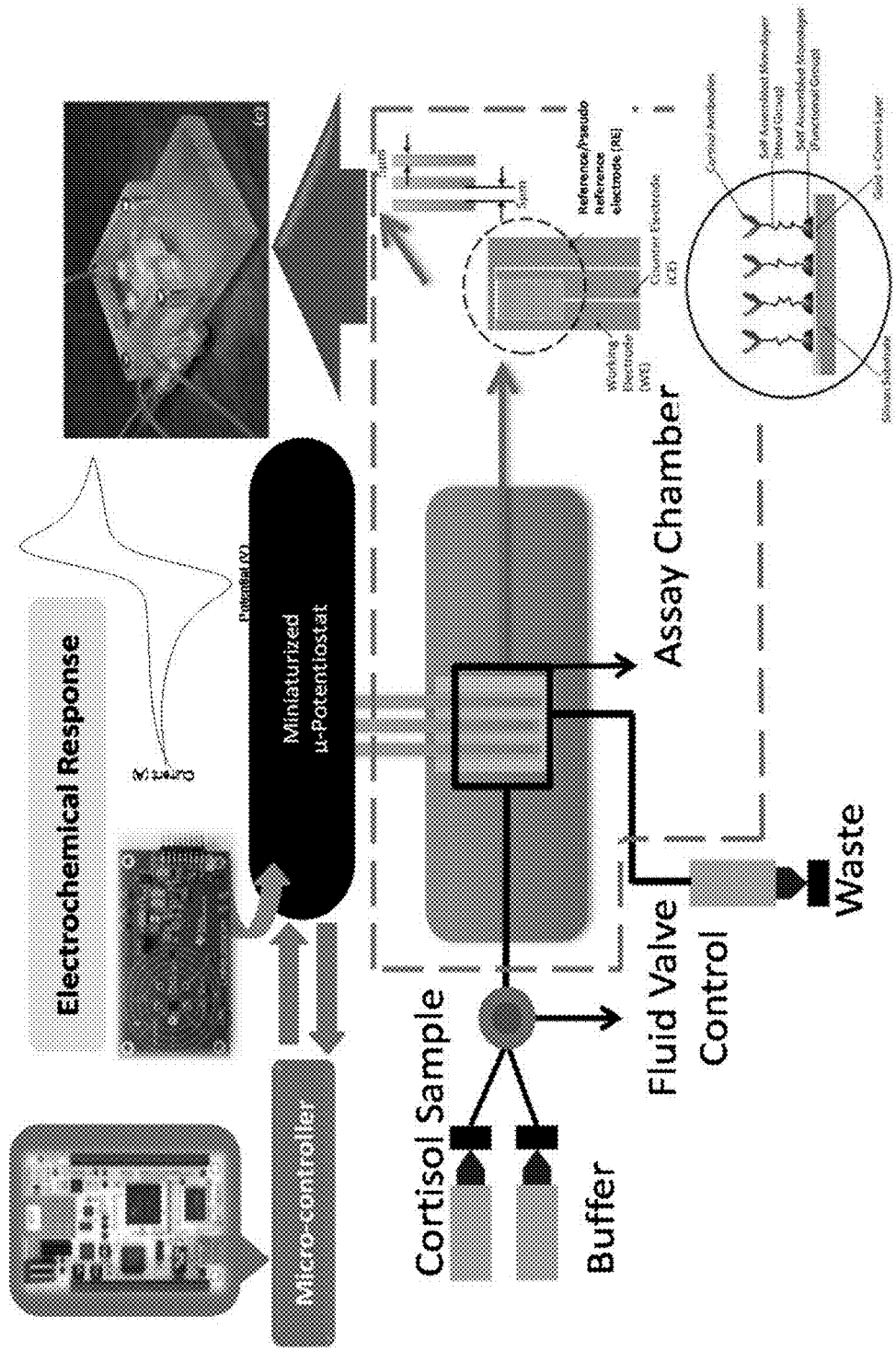
FIG. 33. Block diagram of the miniaturized electrochemical biosensor cortisol detection system and its working.
Figure 34:
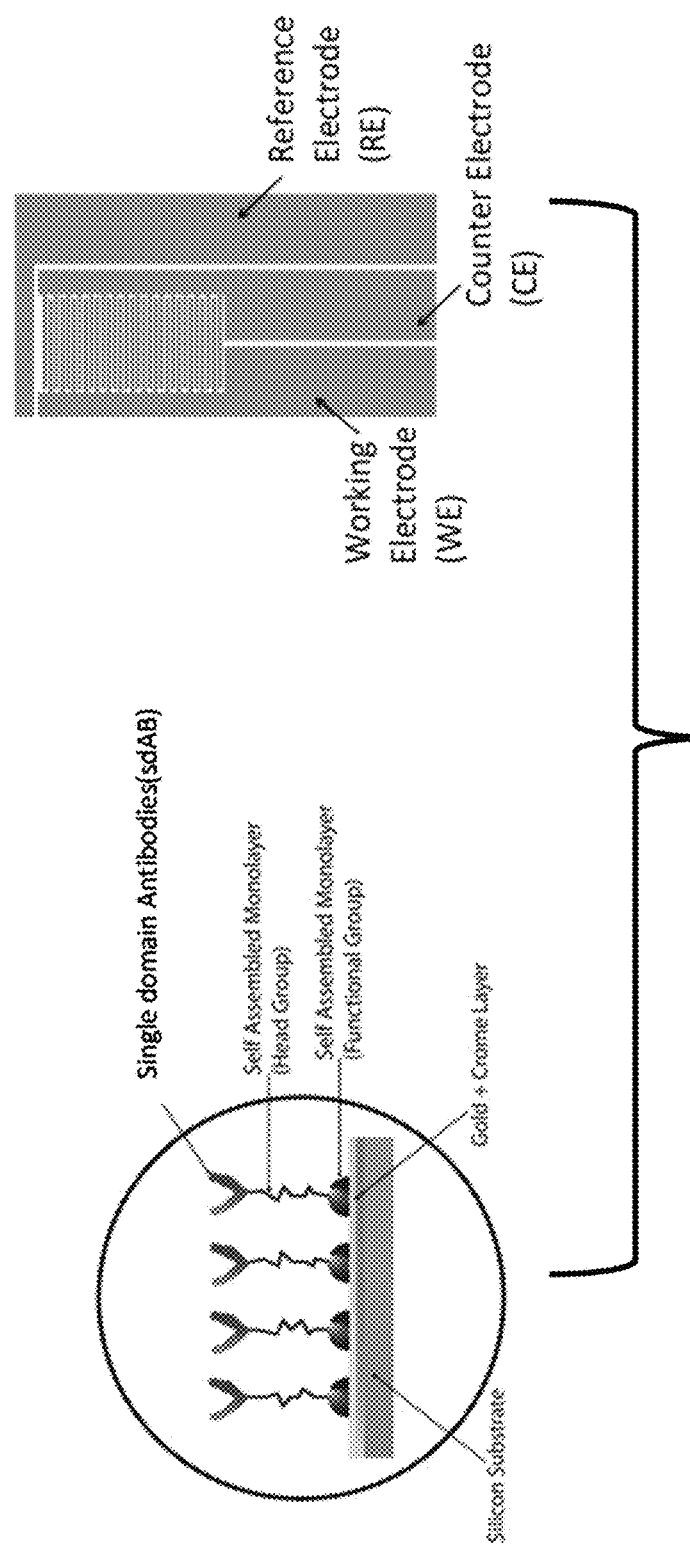
FIG. 34. Electrochemical biosensor of the current invention containing single domain antibodies.

Description of the Electrodes (FIG. 33)

The DTSP-SAM/IDE were incubated with sdAB for 2 hrs followed by carefully washing with PBS (pH 7.4, 10 mM) to remove any unbound molecules. Phosphate buffer saline (PBS) solution (10 mM, pH 7.4) was prepared by dissolving 1 PBS tablet in 200 mL of DI water and used to prepare the sdAB (1 mg/mL) and Ricin solutions. sdAB/DTSP/IDEs were washed with PBS and stored in refrigerator at 4° C. when not in use.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

1. D. L. Delahanty, A. J. Raimonde, and E. Spoonster, Biological Psychiatry, 48, 940 (2000).
2. R. Yehuda, S. L. Halligan, and L. M. Bierer, Psychoneuroendocrinology, 27, 171 (2002).
3. R. Yehuda, S. L. Halligan, and R. Grossman, Development and Psychopathology, 13, 733 (2001).
4. M. Venugopal, S. K. Arya, G. Chornokur, and S. Bhansali, Sensors and Actuators A: Physical, 172, 154 (2011).
5. A. Kaushik, A. Vasudev, S. K. Arya, S. K. Pasha, and S. Bhansali, Biosensors and Bioelectronics, 53, 499 (2014).
6. R. Gatti, G. Antonelli, M. Prearo, P. Spinella, E. Cappellin, and E. F. De Palo, Clinical Biochemistry, 42, 1205 (2009).
7. A. Levine, O. 333 Zagoory-Sharon, R. Feldman, J. G. Lewis, and A. Weller, Physiology & Behavior, 90, 43 (2007).
8. M. J. E. Ron de Kloet and F. Holsboer, Nature Reviews Neuroscience, 6, 13 (2005).
9. B. S. McEwen, Journal of Clinical Endocrinology & Metabolism, 87, 1947 (2002).
10. Z. Djuric, C. E. Bird, A. Furumoto-Dawson, G. H. Rauscher, M. T. Ruffin Iv, R. P. Stowe, K. L. Tucker, and C. M. Masi, The Open Biomarkers Journal, 1, 7 (2008).
11. E. M. Clingerman and A. Brown, Biological Research for Nursing, 14, 27 (2012).
12. A. Cecchi, M. Rovedatti, G. Sabino, and G. Magnarelli, Ecotoxicology and Environmental Safety, 80, 280 (2012).
13. B. J. Klopfenstein, J. Q. Purnell, D. D. Brandon, L. M. Isabelle, and A. E. DeBarber, Clinical Biochemistry, 44, 430 (2011).
14. L.-Q. Chen, X.-J. Kang, J. Sun, J.-J. Deng, Z.-Z. Gu, and Z.-H. Lu, Journal of Separation Science, 33, 2369 (2010).
15. W. Gao, Q. Xie, J. Jin, T. Qiao, H. Wang, L. Chen, H. Deng, and Z. Lu, Clinical Biochemistry, 43, 677 (2010).

16. D. Appel, R. D. Schmid, C.-A. Dragan, M. Bureik, and V. B. Urlacher, Analytical and Bioanalytical Chemistry, 383, 182 (2005).
17. M. O. van Aken, J. A. Romijn, J. A. Miltenburg, and E. G. W. M. Lentjes, Clinical Chemistry, 49, 1408 (2003).
18. C. Carrozza, S. M. Corsello, R. M. Paragliola, F. Ingraudo, S. Palumbo, P. Locantore, A. Sferrazza, A. Pontecorvi, and C. Zuppi, Annals of Clinical Biochemistry, 47, 228 (2010).
19. G. Lippi, F. De Vita, G. L. Salvagno, M. Gelati, M. Montagnana, and G. C. Guidi, Clinical Biochemistry, 42, 904 (2009).
20. M. Yaneva, G. Kirilov, and S. Zacharieva, Central European Journal of Medicine, 4, 59 (2009).
21. H. Shi, X. Xu, Y. Ding, S. Liu, L. Li, and W. Kang, Analytical Biochemistry, 387, 178 (2009).
22. J. Lewis and P. Elder, Journal of Steroid Biochemistry, 22, 673 (1985).
23. L. Manenschijn, J. W. Koper, S. W. J. Lamberts, and E. F. C. van Rossum, Steroids, 76, 1032 (2011).
24. M. Shimada, K. Takahashi, T. Ohkawa, M. Segawa, and M. Higurashi, Hormone Research in Paediatrics, 44, 213 (1995).
25. B. C. Small and K. B. Davis, Journal of the World Aquaculture Society, 33, 184 (2007).
26. J. S. Mitchell, T. E. Lowe, and J. R. Ingram, Analyst, 134, 380 (2008).
27. D. R. Shankaran, K. V. Gobi, and N. Miura, Sensors and Actuators B: Chemical, 121, 158 (2007).
28. R. C. Stevens, S. D. Soelberg, S. Near, and C. E. Furlong, Analytical Chemistry, 80, 6747 (2008).
29. M. Z. Atashbar, B. Bejcek, A. Vijh, and S. Singamaneni, Sensors and Actuators B: Chemical, 107, 945 (2005).
30. E. Aardal and A.-C. Holm, Clinical Chemistry and Laboratory Medicine, 33, 927 (1995).
31. Y. Wan, Y. Su, X. Zhu, G. Liu, and C. Fan, Biosensors and Bioelectronics, 47, 1 (2013).
32. A. Kaushik, S. K. Arya, A. Vasudev, and S. Bhansali, Journal of Nanoscience Letters J. Nanosci. Lett, 3, 32 (2013).
33. C. Loncaric, Y. Tang, C. Ho, M. A. Parameswaran, and H.-Z. Yu, Sensors and Actuators B: Chemical, 161, 908 (2012).
34. P. B. Lillehoj, M.-C. Huang, N. Truong, and C.-M. Ho, Lab on a Chip, 13, 2950 (2013).
35. S. K. Arya, G. Chornokur, M. Venugopal, and S. Bhansali, Biosensors and Bioelectronics, 25, 2296 (2010).
36. S. K. Arya, G. Chornokur, M. Venugopal, and S. Bhansali, The Analyst, 135, 1941 (2010).
37. A. Kumar, S. Aravamudhan, M. Gordic, S. Bhansali, and S. S. Mohapatra, Biosensors and Bioelectronics, 22, 2138 (2007).
38. S. K. Arya, A. Dey, and S. Bhansali, Biosensors and Bioelectronics, 28, 166 (2011).
39. A. Kaushik, A. Vasudev, S. K. Arya, and S. Bhansali, Biosensors and Bioelectronics, 50, 35 (2013).
40. M. Yamaguchi, Y. Matsuda, S. Sasaki, M. Sasaki, Y. Kadoma, Y. Imai, D. Niwa, and V. Shetty, Biosensors and Bioelectronics, 41, 186 (2013).
41. K. Fujiwara, E. Tsukishima, S. Kasai, A. Masuchi, A. Tsutsumi, N. Kawakami, H. Miyake, and R. Kishi, Scandinavian Journal of work, Environment and Health, 30, 129 (2004). Q4 401
42. G. Lac and A. Chamoux, Occupational Medicine, 53, 143 (2003).
43. N. Lamond, J. Dorrian, G. D. Roach, K. McCulloch, A. Holmes, H. J. Burgess, A. Fletcher, and D. Dawson, Occupational and Environmental Medicine, 60, e13 (2003).
44. S. C. Carvajal, C. Kibor, D. J. McClelland, M. Ingram, J. G. de Zapien, E. Torres, F. Redondo, K. Rodriguez, R. Rubio-Goldsmith, and J. Meister, Journal of Immigrant and Minority Health, 1 (2013).
45. J. Fischer, A. Calame, A. Dettling, H. Zeier, and S. Fanconi, International Archives of Occupational and Environmental Health, 73, S46 (2000).
46. U. Lundberg and B. Hellström, Work and Stress, 16, 356 (2002).
47. D. Mangold, G. Wand, M. Javors, and J. Mintz, Hormones and Behavior, 58, 637 (2010).
48. D. Mangold, E. Marino, and M. Javors, Journal of Psychiatric Research, 45, 902 (2011).
49. V. Anandan, Y. L. Rao, and G. Zhang, International Journal of Nanomedicine, 1, 73 (2006).
50. T. J. Kindt and J. Kuby, Kuby immunology, Macmillan (2007).
51. J. Wang, Electrochemical biosensors: towards point-of-care cancer diagnostics, Biosensors and Bioelectronics 21 (10) (2006) 1887-1892.
52. G. M. Whitesides, The origins and the future of microfluidics, Nature 442 (7101) (2006) 368-373.
53. M. R. Gongora-Rubio, et al., Overview of low temperature co-fired ceramics tape technology for meso-system technology (MsST), Sensors and Actuators A: Physical 89 (3) (2001) 222-241.
54. K. A. Peterson, et al., Novel microsystem applications with new techniques in low-temperature co-fired ceramics, International Journal of Applied Ceramic Technology 2 (5) (2005) 345-363.
55. A. Vasudev, et al., Prospects of low temperature co-fired ceramic (LTCC) based microfluidic systems for point-of-care biosensing and environmental sensing, Microfluidics and Nanofluidics 14 (3-4) (2012) 683-702.
56. P. Bembnowicz, et al., Preliminary studies on LTCC based PCR microreactor, Sensors and Actuators B: Chemical 150 (2) (2010) 715-721.
57. P. Ciosek, et al., Monitoring of cell cultures with LTCC microelectrode array, Analytical and Bioanalytical Chemistry 393 (8) (2009) 2029-2038.
58. N. Ibánez-García, et al., Green-tape ceramics. New technological approach for integrating electronics and fluidics in microsystems, Trends in Analytical Chemistry 27 (1) (2008) 24-33.
59. K. Malecha, et al., LTCC microreactor for urea determination in biological fluids, Sensors and Actuators B: Chemical 141 (1) (2009) 301-308.
60. S. J. Lupien, et al., Effects of stress throughout the lifespan on the brain: behaviour and cognition, Nature Reviews Neuroscience 10 (6) (2009) 434-445.
61. D. H. Hellhammer, S. Wüst, B. M. Kudielka, Salivary cortisol as a biomarker in stress research, Psychoneuroendocrinology 34 (2) (2009) 163-171.
62. E. F. De Palo, et al., Human saliva cortisone and cortisol simultaneous analysis using reverse phase HPLC technique, Clinica Chimica Acta 405 (1-2) (2009) 60-65.
63. M. Vogeser, P. Möhnle, J. Briegel, Free serum cortisol: quantification applying equilibrium dialysis or ultrafiltration and an automated immunoassay system, Clinical Chemical Laboratory Medicine 45 (4) (2007) 521.
64. L. Gervais, N. de Rooij, E. Delamarche, Microfluidic chips for point-of-care immunodiagnostics, Advanced Materials 23 (24) (2011) H151-H176.

65. K. Malecha, L. J. Golonka, CFD simulations of LTCC based microsystems, in: ISSE'06. 29th International Spring Seminar on Electronics Technology 2006, 2006.
66. K. Malecha, et al., Low temperature co-fired ceramic (LTCC)-based biosensor for continuous glucose monitoring, Sensors and Actuators B: Chemical 155 (2) (2011) 923-929.
67. H. Birol, T. Maeder, P. Ryser, Application of graphite-based sacrificial layers for fabrication of LTCC (low temperature co-fired ceramic) membranes and microchannels, Journal of Micromechanics and Microengineering 17 (1) (2007) 50.
68. M. Farhan Shafique, et al., Fabrication of embedded microfluidic channels in low temperature co-fired ceramic technology using laser machining and progressive lamination, Journal of the European Ceramic Society 31 (13) (2011) 2199-2204.
69. F. Barlow, et al., Fabrication of precise fluidic structures in LTCC, International Journal of Applied Ceramic Technology 6 (1) (2009) 18-23.
70. P. Bembnowicz, D. Nowakowska, L. Golonka, Integrated LTCC-glass microreactor and µTAS with thermal stabilization for biological application, in: Microelectronics and Packaging Conference, 2009. EMPC 2009. European, 2009.

What is claimed is:

1. An electrochemical biosensor for measuring concentration of an analyte in a fluid, the electrochemical biosensor comprising:
    a) a sensing electrode having deposited onto its surface a polyaniline (PANI)-silver-silver oxide core-shell (Ag@AgO) nanocomposite that immobilizes a binding agent capable of specifically binding to the analyte to form a binding agent-analyte complex and wherein the binding of the analyte to the binding agent causes electron transfer resistance at the sensing electrode surface thereby providing a change in the electrochemical response at the sensing electrode surface proportional to the number of binding agent-analyte complexes,
    b) a detection solution comprising a soluble redox probe, and
    c) a test equipment capable of measuring the electrochemical response at the sensing electrode surface.

2. The electrochemical biosensor of claim 1, wherein the sensing electrode is fabricated from a noble metal.

3. The electrochemical biosensor of claim 2, wherein the noble metal is copper, silver, platinum, gold, bismuth, palladium, osmium, iridium, ruthenium, and rhodium.

4. The electrochemical biosensor of claim 1, wherein the binding agent is a binding protein, an antibody, or an aptamer that specifically binds to the analyte and the analyte is a biomolecule.

5. The electrochemical biosensor of claim 4, wherein the biomolecule is a hormone, a protein, a polysaccharide, a lipid, a polynucleotide, or a metabolite.

6. The electrochemical biosensor of claim 5, wherein the hormone is a peptide hormone or a steroid hormone.

7. The electrochemical biosensor of claim 6, wherein the peptide hormone is selected from Thyroid-stimulating hormone (TSH), Follicle-stimulating hormone (FSH), Luteinizing hormone (LH), Prolactin (PRL), Growth hormone (GH), Adrenocorticotropic hormone (ACTH), Vasopressin, Oxytocin, Thyrotropin-releasing hormone (TRH), Gonadotropin-releasing hormone (GnRH), Growth hormone-releasing hormone (GHRH), Corticotropin-releasing hormone (CRH), Somatostatin, Calcitonin, Parathyroid hormone (PTH), FGF-23 (phosphatonin), Osteocalcin, Erythropoietin (EPO), Human chorionic gonadotropin (HCG), Insulin, Glucagon, Amylin, Atrial-natriuretic peptide (ANP), Gastrin, Secretin, Cholecystokinin (CCK), Fibroblast Growth Factor 19 (FGF19), Neuropeptide Y, Ghrelin, PYY3-36, Insulin-like growth factor-1 (IGF-1), Angiotensinogen, Thrombopoietin, Hepcidin, Betatrophin, Leptin, Retinol Binding Protein 4, Adiponectin, and Irisin.

8. The electrochemical biosensor of claim 6, wherein the steroid hormone is selected from progesterone, aldosterone, testosterone, estradiol, and cortisol.

9. The electrochemical biosensor of claim 1, wherein the soluble redox probe is ferro-ferri cyanide.

10. A method of measuring concentration of an analyte in a fluid, the method comprising:
    a) providing an electrochemical biosensor comprising:
        A) a sensing electrode having deposited onto its surface a polyaniline (PANI)-silver-silver oxide core-shell (Ag@AgO) nanocomposite that immobilizes a binding agent capable of specifically binding to the analyte form a binding agent-analyte complex and wherein the binding of the analyte to the binding agent causes electron transfer resistance at the sensing electrode surface thereby providing a change in the electrochemical response at the sensing electrode surface proportional to the number of binding agent-analyte complexes,
        B) a detection solution comprising a soluble redox probe, and
        C) a test equipment which measures the electrochemical response at the sensing electrode surface,
    b) contacting the sensing electrode with the fluid under conditions that allow the formation of the binding agent-analyte complexes for a period of time sufficient to allow the formation of the binding agent-analyte complexes,
    c) washing the sensing electrode with a washing solution to remove unbound and non-specifically bound chemicals from the sensing electrode,
    d) introducing a detection solution over the sensing electrode,
    e) measuring the electrochemical response at the sensing electrode surface, and
    f) calculating the concentration of the analyte in the fluid based on the electrochemical response at the sensing electrode surface.

11. The method of claim 10, wherein the binding agent is a binding protein, an antibody, or an aptamer that specifically binds to the analyte and the analyte is a biomolecule.

12. The method of claim 11, wherein the biomolecule is a protein, a hormone, or a metabolite.

13. The method of claim 12, wherein the hormone is a peptide hormone or a steroid hormone.

14. The method of claim 13, wherein the peptide hormone is selected from TSH, FSH, LH, PRL, GH, ACTH, Vasopressin, Oxytocin, TRH, GnRH, GHRH, CRH, Somatostatin, Calcitonin, PTH, FGF-23, Osteocalcin, EPO, HCG, Insulin, Glucagon, Amylin, ANP, Gastrin, Secretin, CCK, FGF19, Neuropeptide Y, Ghrelin, PYY3-36, IGF-1, Angiotensinogen, Thrombopoietin, Hepcidin, Betatrophin, Leptin, Retinol Binding Protein 4, Adiponectin, and Irisin.

15. The method of claim 13, wherein the steroid hormone is selected from progesterone, aldosterone, testosterone, estradiol, and cortisol.

16. The method of claim 10, wherein the soluble redox probe is ferro-ferri cyanide.

17. A method of detecting the presence of a cortisol-related chronic condition in a subject, the method comprising:
a) providing an electrochemical biosensor comprising:
A) a sensing electrode having attached to its surface a binding agent capable of specifically binding to cortisol to form a binding agent-cortisol complex and wherein the binding of cortisol to the binding agent causes electron transfer resistance at the sensing electrode surface thereby providing a change in the electrochemical response at the sensing electrode surface proportional to the number of binding agent-cortisol complexes, B) a detection solution comprising a soluble redox probe, and
C) a test equipment which measures the electrochemical response at the sensing electrode surface,
b) contacting the sensing electrode with the biofluid under conditions that allow the formation of the binding agent-cortisol complexes for a period of time sufficient to allow the formation of the binding agent-cortisol complexes,
c) washing the sensing electrode with a washing solution to remove unbound and non-specifically bound chemicals from the sensing electrode,
d) introducing a detection solution over the sensing electrode,
e) measuring the electrochemical response at the sensing electrode surface,
f) calculating the concentration of cortisol in the biofluid based on the electrochemical response at the sensing electrode surface, and
g) identifying the subject as having a cortisol-related chronic condition;
if the concentration of cortisol in the biofluid is higher or lower than the concentration of cortisol in the biofluid of a subject not having the cortisol-related chronic condition, wherein the biofluid of the subject and the subject not having the cortisol-related chronic condition are collected at similar times of day.

18. The method of claim 17, wherein the binding agent is a binding protein, an antibody, or an aptamer that specifically binds to cortisol.

19. The method of claim 17, wherein the soluble redox probe is ferro-ferri cyanide.

* * * * *